(12) United States Patent
Choren

(10) Patent No.: US 9,034,048 B2
(45) Date of Patent: May 19, 2015

(54) ORTHOPAEDIC IMPLANTS AND METHODS OF FORMING IMPLANT STRUCTURES

(76) Inventor: John A. Choren, Oconomowoc, WI (US)

( * ) Notice: Subject to any disclaimer, the term of this patent is extended or adjusted under 35 U.S.C. 154(b) by 66 days.

(21) Appl. No.: 13/358,207

(22) Filed: Jan. 25, 2012

(65) Prior Publication Data

US 2012/0191200 A1 Jul. 26, 2012

Related U.S. Application Data

(60) Provisional application No. 61/436,459, filed on Jan. 26, 2011.

(51) Int. Cl.
*A61F 2/30* (2006.01)
*A61F 2/36* (2006.01)
*A61F 2/32* (2006.01)

(52) U.S. Cl.
CPC ............... *A61F 2/3662* (2013.01); *Y10T 29/49* (2015.01); *A61F 2/3094* (2013.01); *A61F 2/32* (2013.01); *A61F 2002/3092* (2013.01); *A61F 2002/30968* (2013.01); *A61F 2002/3097* (2013.01); *A61F 2002/30733* (2013.01)

(58) Field of Classification Search
USPC ............ 623/18.11, 16.11, 11.11, 23.5–23.55, 623/23.6, 23.7–23.76; 424/443; 427/2.26, 427/2.27
See application file for complete search history.

(56) References Cited

U.S. PATENT DOCUMENTS

| | | | | |
|---|---|---|---|---|
| 3,848,273 A * | 11/1974 | Frey | | 623/23.29 |
| 3,852,045 A * | 12/1974 | Wheeler et al. | | 428/566 |
| 4,595,393 A * | 6/1986 | Anapliotis et al. | | 623/23.33 |
| 4,608,052 A * | 8/1986 | Van Kampen et al. | | 623/23.29 |
| 4,978,358 A * | 12/1990 | Bobyn | | 623/23.34 |
| 5,015,817 A * | 5/1991 | Kranz | | 219/121.14 |
| 5,021,063 A * | 6/1991 | Tager | | 623/23.33 |
| 5,141,521 A * | 8/1992 | Wenner | | 623/23.34 |
| 5,152,798 A * | 10/1992 | Kranz | | 623/23.33 |
| 5,156,628 A * | 10/1992 | Kranz | | 623/23.33 |
| 5,180,395 A * | 1/1993 | Klaue | | 623/23.34 |
| 5,181,930 A * | 1/1993 | Dumbleton et al. | | 623/23.34 |
| 5,192,330 A * | 3/1993 | Chang et al. | | 623/23.34 |
| 5,219,363 A * | 6/1993 | Crowninshield et al. | | 623/23.34 |
| 5,226,917 A * | 7/1993 | Schryver | | 623/22.37 |
| 5,310,408 A * | 5/1994 | Schryver et al. | | 623/22.37 |
| 5,314,492 A * | 5/1994 | Hamilton et al. | | 623/23.34 |
| 5,330,536 A * | 7/1994 | Tager et al. | | 623/23.33 |
| 5,455,100 A * | 10/1995 | White | | 428/131 |
| 5,879,398 A * | 3/1999 | Swarts et al. | | 623/22.21 |
| 6,302,913 B1 * | 10/2001 | Ripamonti et al. | | 623/16.11 |
| 6,306,169 B1 * | 10/2001 | Lee et al. | | 623/11.11 |
| 6,306,424 B1 * | 10/2001 | Vyakarnam et al. | | 424/426 |
| 6,312,473 B1 * | 11/2001 | Oshida | | 623/23.55 |
| 6,361,565 B1 * | 3/2002 | Bonutti | | 623/22.12 |

(Continued)

OTHER PUBLICATIONS

Karrholm, J., Anderberg, C., Snorrason, F., et al., Evaluation of a Femoral Stem with Reduced Stiffness, Journal of Bone and Joint Surgery, vol. 84-A, No. 9, pp. 1651-1658, 2002.

(Continued)

*Primary Examiner* — Alvin Stewart

(74) *Attorney, Agent, or Firm* — Ryan Kromholz & Manion, S.C.

(57) ABSTRACT

Additive processes and novel implant designs provide precise pore design and positioning for clinically useful microstructures exhibiting the appropriate rigidity for orthopaedic implants.

9 Claims, 9 Drawing Sheets

(56) References Cited

U.S. PATENT DOCUMENTS

| | | | |
|---|---|---|---|
| 6,524,344 B2* | 2/2003 | Yoon | 623/23.46 |
| 6,737,149 B1* | 5/2004 | Wintermantel et al. | 428/131 |
| 6,786,932 B1* | 9/2004 | Blackmore | 623/23.33 |
| 6,846,327 B2* | 1/2005 | Khandkar et al. | 623/16.11 |
| 6,949,123 B2* | 9/2005 | Reiley | 623/17.11 |
| 7,077,867 B1* | 7/2006 | Pope et al. | 623/20.14 |
| 7,122,057 B2* | 10/2006 | Beam et al. | 623/23.51 |
| 7,648,735 B2* | 1/2010 | Hunter et al. | 427/248.1 |
| 7,682,540 B2* | 3/2010 | Boyan et al. | 264/212 |
| 7,749,555 B2* | 7/2010 | Zanella et al. | 427/2.26 |
| 7,806,911 B2* | 10/2010 | Peckham | 606/248 |
| 7,909,883 B2* | 3/2011 | Sidebotham | 623/23.55 |
| 8,080,483 B2* | 12/2011 | Hillhouse et al. | 438/780 |
| 8,221,477 B2* | 7/2012 | Aeschlimann et al. | 606/300 |
| 8,252,570 B2* | 8/2012 | Harlow et al. | 435/175 |
| 8,287,915 B2* | 10/2012 | Clineff et al. | 424/602 |
| 2001/0053937 A1* | 12/2001 | Johnson et al. | 623/23.34 |
| 2002/0120338 A1* | 8/2002 | Boyer et al. | 623/17.19 |
| 2003/0009225 A1* | 1/2003 | Khandkar et al. | 623/17.16 |
| 2005/0015088 A1* | 1/2005 | Ringeisen | 606/69 |
| 2005/0027366 A1* | 2/2005 | Saini et al. | 623/23.5 |
| 2005/0049715 A1* | 3/2005 | Ito et al. | 623/23.5 |
| 2005/0085817 A1* | 4/2005 | Ringeisen | 606/69 |
| 2005/0102036 A1* | 5/2005 | Bartee et al. | 623/23.76 |
| 2005/0112397 A1* | 5/2005 | Rolfe et al. | 428/593 |
| 2005/0177238 A1* | 8/2005 | Khandkar et al. | 623/17.11 |
| 2005/0187638 A1* | 8/2005 | Glien et al. | 623/23.56 |
| 2005/0196452 A1* | 9/2005 | Boyan et al. | 424/486 |
| 2005/0288790 A1* | 12/2005 | Swords | 623/17.19 |
| 2006/0030851 A1* | 2/2006 | Bray et al. | 606/69 |
| 2006/0224242 A1* | 10/2006 | Swords et al. | 623/17.19 |
| 2006/0229715 A1* | 10/2006 | Istephanous et al. | 623/1.46 |
| 2006/0276925 A1* | 12/2006 | Lin et al. | 700/118 |
| 2007/0116734 A1* | 5/2007 | Akash | 424/423 |
| 2007/0129809 A1* | 6/2007 | Meridew et al. | 623/22.32 |
| 2007/0134216 A1* | 6/2007 | Harlow et al. | 424/93.21 |
| 2007/0150068 A1* | 6/2007 | Dong et al. | 623/22.32 |
| 2007/0173950 A1* | 7/2007 | Zanella et al. | 623/23.63 |
| 2008/0133026 A1* | 6/2008 | Lei et al. | 623/23.54 |
| 2008/0288083 A1* | 11/2008 | Axelsson et al. | 623/23.51 |
| 2009/0112315 A1* | 4/2009 | Fang et al. | 623/11.11 |
| 2009/0157182 A1* | 6/2009 | Koblish et al. | 623/16.11 |
| 2009/0162235 A1* | 6/2009 | Kita et al. | 419/2 |
| 2009/0192610 A1* | 7/2009 | Case et al. | 623/16.11 |
| 2010/0075419 A1* | 3/2010 | Inagaki et al. | 435/402 |
| 2010/0137990 A1* | 6/2010 | Apatsidis et al. | 623/17.16 |
| 2010/0222892 A1* | 9/2010 | Linares | 623/23.5 |
| 2011/0014289 A1* | 1/2011 | Datta et al. | 424/486 |
| 2011/0022180 A1* | 1/2011 | Melkent et al. | 623/23.5 |
| 2011/0022181 A1* | 1/2011 | Kasahara et al. | 623/23.5 |
| 2011/0027181 A1* | 2/2011 | Amodei et al. | 424/9.1 |
| 2011/0064784 A1* | 3/2011 | Mullens et al. | 424/443 |
| 2011/0125284 A1* | 5/2011 | Gabbrielli et al. | 623/23.4 |
| 2011/0278533 A1* | 11/2011 | Hillhouse et al. | 257/9 |
| 2012/0022662 A1* | 1/2012 | Conway et al. | 623/22.21 |
| 2012/0184960 A1* | 7/2012 | Dosta | 606/71 |
| 2013/0138155 A1* | 5/2013 | Hoornaert et al. | 606/283 |

OTHER PUBLICATIONS

Engh, C.A., Bobyn, J.D., The Influence of Stem Size and Extent of Porous Coating on Femoral Bone Resorption after Primary Cementless Hip Arthroplasty, Clinical Orthopaedics and Related Research, vol. 231, pp. 7-28, 1988.

Engh, C.A., Young, A.M., Engh, C.A. Sr., Hopper, R.H., Clinical Consequences of Stress Shielding After Porous-Coated Total Hip Arthroplasty, Clinical Orthopaedics and Related Research, vol. 417, pp. 157-163, 2003.

Huiskes, R., Boeklagen, R., Mathematical Shape Optimization of Hip Prosthesis Design, Journal of Biomechanics, vol. 22, No. 8/9, pp. 793-804, 1989.

Nistor, L., Blaha, J.D., et al., In Vivo Measurements of Relative Motion between an Uncemented Femoral Total Hip Component and the Femur by Roentgen Stereophotogrammetric Analysis, Clinical Orthopaedics and Related Research, vol. 269, pp. 220-227, 1991.

Bugbee, W.D., Culpepper, W.J., Engh, C.A. Jr., Engh, C.A. Sr., Long-Term Clinical Consequences of Stress-Shielding after Total Hip Arthroplasty without Cement, Journal of Bone and Joint Surgery, vol. 79, No. 7, pp. 1007-1012, 1997.

Kuiper, J.H., Huiskes, R., Mathematical Optimization of Elastic Properties: Application to Cementless Hip Stem Design, Journal of Biomechanical Engineering, vol. 119, No. 2, pp. 166-174, 1997.

Joshi, M.G., Santare, M.H., Advani, S.G., Survey of stress analyses of the femoral hip prosthesis, ASME Applied Mechanical Review, vol. 53, No. 1, pp. 1-18, 2000.

Gruen, T.A., McNeice, G.M., Amstutz, H.C., "Modes of Failure" of Cemented Stem-type Femoral Components, Clinical Orthopaedics and Related Research, vol. 141, pp. 17-27, 1979.

Engh, C.A., Claus, A.M., Hopper, R.H., Engh, C.A., Long-Term Results Using Anatomic Medullary Locking Hip Prosthesis, Clinical Orthopaedics and Related Research, vol. 393, pp. 137-146, 2001.

Au, M.K., Isoelastic Total Hip Replacement: Critical Evaluation of Prosthetic Isoelasticity, Journal of the Formosan Medical Association, vol. 93, No. 6, pp. 497-502, 1994.

Gross, S., Abel, E.W., A finite element analysis of hollow stemmed hip prostheses as a means of reducing stress shielding of the femur, Journal of Biomechanics, vol. 34, pp. 995-1003, 2001.

Skinner, H.B., Isoelasticity and Total Hip Arthroplasty, Orthopedics, vol. 14, No. 3, pp. 323-328, 1991.

Wan, Z., Dorr, L.D., Woodsome, T., Ranawat, A., Song, M., Effect of Stem Stiffness and Bone Stiffness on Bone Remodeling in Cemented Total Hip Replacement, The Journal of Arthroplasty, vol. 14, No. 2, pp. 149-158, 1999.

Weinans, H., Huiskes, R., Van Rietbergen, B., et al., Adaptive Bone Remodeling Around Bonded Noncemented Total Hip Arthroplasty: A Comparison between Animal Experiments and Computer Simulation, Journal of Orthopaedic Research, vol. 11, No. 4, pp. 500-513, 1993.

Joshi, M.G., et al., Analysis of femoral hip prosthesis designed to reduce stress shielding, Journal of Biomechanics, vol. 33, pp. 1655-1662, 2000.

Huiskes, R., Failed innovation in total hip replacement: Diagnosis and proposals for a cure, Acta Orthopaedics Scandinavica, vol. 64, No. 6, pp. 699-716, 1993.

Engh, C.A., O'Connor, D., Jasty, M., et al., Quantification of Implant Micromotion, Strain Shielding and Bone Resorption With Porous-Coated Anatomic Medullary Locking Femoral Prostheses, Clinical Orthopaedics and Related Research, vol. 285, pp. 13-29, 1992.

Weinans, H., Sumner, D., Igloria, R., Natarajan, R., Sensitivity of periprosthetic stress-shielding to load and the bone density-modulus relationship in subject-specific finite element models, Journal of Biomechanics, vol. 33, pp. 809-817, 2000.

Bobyn, J.D., Mortimer, E.S., Glassman, A.H., Engh, C.A., et al., Producing and Avoiding Stress Shielding, Clinical Orthopaedics and Related Research, vol. 274, pp. 79-96, 1992.

Huiskes, R., Nunamaker, D., Local Stresses and Bone Adoption Around Orthopedic Implants, Calcified Tissue International, vol. 36, pp. S110-S117, 1984.

Kilgus, D.J., Shimaoka, E.E., Tipton, J.S., Eberle, R.W., Dual-Energy X-Ray Absorptiometry Measurement of Bone Mineral Density around Porous-Coated Cementless Femoral Implants, Journal of Bone & Joint Surgery (Br), vol. 75-B, No. 2, pp. 279-287, 1993.

Sychterz, C.J., Engh, C.A., The Influence of Clinical Factors on Periprosthetic Bone Remodeling, Clinical Orthopaedics and Related Research, vol. 322, pp. 285-292, 1996.

Lewis, J.L., Askew, M.J., Wixson, R.L. et al., The Influence of Prosthetic Stem Stiffness and of a Calcar Collar on Stresses in the Proximal End of the Femur with a Cemented Femoral Component, Journal of Bone and Joint Surgery, vol. 66-A, No. 2, pp. 280-286, 1984.

Engh, C.A., McGovern, T.F., Bobyn, J.D., Harris, W.H., A Quantitative Evaluation of Periprosthetic Bone-Remodeling After Cementless Total Hip Arthroplasty, Journal of Bone and Joint Surgery, vol. 74, No. 7, pp. 1009-1020, 1992.

Glassman, A., Bobyn, J., Tanzer, M., New Femoral Designs: Do They Influence Stress Shielding?, Clinical Orthopaedics and Related Research, vol. 453, pp. 64-74, 2006.

(56) References Cited

OTHER PUBLICATIONS

Huiskes, R., Weinans, H., Grootenboer, H.J., et al., Adaptive Bone-Remodeling Theory Applied to Prosthetic-Design Analysis, Journal of Biomechanics, vol. 20, No. 11/12, pp. 1135-1150, 1987.

Van Rietbergen, B., Huiskes, R., Weinans, H., et al., The Mechanism of Bone Remodeling and Resorption Around Press-Fitted THA Stems, Journal of Biomechanics, vol. 26, No. 4/5, pp. 369-382, 1993.

Kiratli, B.J., Heiner, J.P., et al, Determination of BMD by Dual X-Ray Absorptiometry in Patients with Uncemented Total Hip Arthroplasty, Journal of Orthopaedic Research, vol. 10, No. 6, pp. 836-844, 1992.

Huiskes, R., Weinans, H., Van Rietbergen, B., The Relationship Between Stress Shielding and Bone Resorption Around Total Hip Stems and the Effects of Flexible Materials, Clinical Orthopaedics and Related Research, vol. 274, pp. 124-134, 1992.

Huiskes, R., Stress Shielding and Bone Resorption in THA: Clinical Versus Computer-Simulation Studies, Acta Orthopaedica Belgica, vol. 59, Suppl. 1, pp. 118-129, 1993.

Brown, I.W., Ring, P.A., Osteolytic Changes in the Upper Femoral Shaft Following Porous-Coated Hip Replacement, Journal of Bone & Joint Surgery (Br), vol. 67-B, No. 2, pp. 218-221, 1985.

Engh, C.A. Jr., Sychterz, C., Engh, C. Sr., Factors Affecting Femoral Bone Remodeling After Cementless Total Hip Arthroplasty, The Journal of Arthroplasty, vol. 14, No. 5, pp. 637-644, 1999.

Namba, R.S., Keyak, J.H., Kim, A.S. et al., Cementless Implant Composition and Femoral Stress, Clinical Orthopaedics and Related Research, vol. 347, pp. 261-267, 1998.

Glassman, A.H., Crowninshield, R.D., et al., A Low Stiffness Composite Biologically Fixed Prosthesis, Clinical Orthopaedics and Related Research, vol. 393, pp. 128-135, 2001.

Skinner, H.B., Curlin, F.J., Decreased Pain with Lower Flexural Rigidity of Uncemented Femoral Prostheses, Orthopedics, vol. 13, No. 11, pp. 1223-1228, 1990.

Dujovne, A. R., Bobyn, J. D., et al., Mechanical Compatibility of Noncemented Hip Prostheses with the Human Femur, The Journal of Arthroplasty, vol. 8, No. 1, pp. 7-22, 1993.

Cameron, H.U., The 3-6 Year Results of a Modular Noncemented Low-bending Stiffness Hip Implant, Journal of Arthroplasty, vol. 8, No. 3, pp. 239-243, 1993.

Sumner, D.R., Galante, J.O., Determinants of Stress Shielding: Design Versus Materials Versus Interface, Clinical Orthopaedics and Related Research, vol. 274, pp. 202-212, 1992.

Huo, M.H., Brown, B.S., What's New in Hip Arthroplasty?, Journal of Bone and Joint Surgery, vol. 85-A, No. 9, pp. 1852-1866, 2003.

Keaveny, T.M., Bartel, D.L., Effects of Porous Coating and Collar Support on Early Load Transfer for a Cementless Hip Prosthesis, Journal of Biomechanics, vol. 26, No. 10, pp. 1205-1216, 1993.

Keaveny, T.M., Bartel, D.L., Effects of Porous Coating, with and without Collar Support, on Early Relative Motion for a Cementless Hip Prosthesis, Journal of Biomechanics, vol. 26, No. 12, pp. 1355-1368, 1993.

Maistrelli, G.L., Fornasier, V., Binnington, A., et al., Effect of Stem Modulus in a Total Hip Arthroplasty Model, Journal of Bone and Joint Surgery (Br), vol. 73-B, pp. 43-46, 1991.

Turner, T.M., Sumner, D.R., et al., Maintenance of Proximal Cortical Bone with Use of a Less Stiff Femoral Component in Hemiarthroplasty of the Hip without Cement, Journal of Bone and Joint Surgery, vol. 79-A, No. 9, pp. 1381-1390, 1997.

Skinner, H.B., Kilgus, D.J., et al., Correlation of Computed Finite Element Stresses to Bone Density after Remodeling around Cementless Femoral Implants, Clinical Orthopaedics and Related Research, vol. 305, pp. 178-179, 1994.

McAuley, J.P., Sychterz, C.J., Engh, C.A., Influence of Porous Coating Level on Proximal Femoral Remodeling, Clinical Orthopaedics and Related Research, vol. 371, pp. 146-153, 2000.

Bobyn, J., Glassman, A., Goto, H., et al., The Effect of Stem Stiffness on Femoral Bone Resorption after Canine Porous-coated Total Hip Arthroplasty, Clinical Orthopaedics and Related Research, vol. 261, pp. 196-213, 1990.

Engh, C.A., Bobyn, J.D., Glassman, A.H., Porous-coated Hip Replacement: The Factors Governing Bone Ingrowth, Stress Shielding, and Clinical Results, Journal of Bone & Joint Surgery (Br), vol. 69-B, No. 1, pp. 45-55, 1987.

Harvey, E.J., Bobyn, J.D., Tanzer, M. et al., Effect of Flexibility of the Femoral Stem on Bone-Remodeling and Fixation of the Stem in a Canine Total Hip Arthroplasty Model without Cement, Journal of Bone and Joint Surgery, vol. 81-A, No. 1, pp. 93-107, 1999.

Simõ, J.A., Monteiro, J., Vaz, M.A., Numerical-Experimental Method for the Validation of a Controlled Stiffness Femoral Prosthesis, Journal of Biomechanical Engineering, vol. 123, pp. 234-238, 2001.

Trebse, R., Milosev, I., et al., Poor results from the Isoelastic total hip replacement: 14-17 year follow-up of 149 cementless prostheses, Acta Orthopaedica, vol. 76, No. 2, pp. 169-176, 2005.

Morscher, E.W., Dick, W., Cementless Fixation of "Isoelastic" Hip Endoprostheses Manufactured from Plastic Materials, Clinical Orthopaedics and Related Research, vol. 176, pp. 77-87, 1983.

Andrew, T., Flanagan, J., Gerundini, M., Bombelli, R., The Isoelastic, Noncemented Total Hip Arthroplasty: Preliminary Experience with 400 Cases, Clinical Orthopaedics and Related Research, vol. 206, pp. 127-138, 1986.

Morscher, E., Bombelli, R., et al., The Treatment of Femoral Neck Fractures with an Isoelastic Endoprosthesis Implanted Without Bone Cement, Archives of Orthopaedic and Trauma Surgery, vol. 98, No. 2, pp. 93-100, 1981.

Bombelli, R., Mathys, R., Cementless Isoelastic RM total hip prosthesis, Journal of the Royal Society of Medicine, vol. 75, pp. 588-597, 1982.

Ang, K. C., Das De, S., Goh, J. C. H., Periprosthetic Bone Remodeling After Cementless Total Hip Replacement, Journal of Bone & Joint Surgery (Br), vol. 79-B, pp. 675-679, 1997.

Museru, L.M., Tay, B. K., Balachandran, N., Isoelastic Cementless Total Hip Replacement Preliminary Results of 24 Replacements, Singapore Medical Journal, vol. 29, No. 4, pp. 361-366, 1988.

Niinimaki, T. J., Puranen, J.P., Jalovaara, P K., Total Hip Arthroplasty Using Isoelastic Femoral Stems: A Seven- to Nine-Year Follow-Up in 108 Patients, Journal of Bone & Joint Surgery (Br), vol. 76-B, pp. 413-418, 1994.

Matricali, G. A., Thibaut, H., Hendrickx, M., Thibaut, R., Revision of Total Hip Arthroplasty Using the R.M. Isoelastic Prosthesis, Acta Orthopaedics Belgica, vol. 59, Suppl. 1, pp. 374-376, 1993.

Ali, M.S., Kumar, A., Isoelastic femoral component in primary cementless total hip arthroplasty, International Orthopaedics, vol. 26, pp. 243-246, 2002.

Jakim, I., Barlin, C., Sweet, M.B.E., RM Isoelastic Total Hip Arthroplasty: A Review of 34 Cases, Journal of Arthroplasty, vol. 3, No. 3, pp. 191-199, 1988.

Schmidt, J., Hackenbroch, M. H., The Cenos hollow stem in total hip arthroplasty: first experiences in a prospective study, Archives of Orthopaedic and Trauma Surgery, vol. 113, No. 3, pp. 117-120, 1994.

Viceconti, M., Toni, A., Giunti, A., Effects of some technological aspects on the fatigue strength of a cementless hip stem, Journal of Biomedical Materials Research, vol. 29, pp. 875-881, 1995.

Engelhardt, J.A., Saha, S., Effect of femoral component section modulus on the stress distribution in the proximal human femur, Medical & Biological Engineering & Computing, vol. 26, pp. 38-45, 1988.

Täger, K.H., The New Spongiosa-Hip-Joint-Endoprosthesis (SHEP), Acta Ortopaedica Belgica, vol. 59, Suppl. 1, pp. 351-353, 1993.

Butel, J., Robb, J. E., The isoelastic hip prosthesis followed for 5 years, Acta Orthopaedica Scandinavica, vol. 59, No. 3, pp. 258-262, 1988.

Jacobsson, S-A., Djerf, K., Gillquist, J., et al., A Prospective Comparison of Butel and PCA Hip Arthroplasty, Journal of Bone & Joint Surgery (Br), vol. 75-B, pp. 624-629, 1993.

Akhavan, S., Matthiesen, M., et al., Clinical and Histologic Results Related to a Low-modulus Composite Total Hip Replacement Stem, Journal of Bone and Joint Surgery, vol. 88-A, No. 6, pp. 1308-1314, 2006.

Simões, J.A., Marques, A.T., Jeronimidis, G., Design of a controlled-stiffness composite proximal femoral prosthesis, Composites Science and Technology, vol. 60, pp. 559-567, 2000.

(56) References Cited

OTHER PUBLICATIONS

Hollister, S.J., Fyhrie, D.P., et al., Application of Homogenization Theory to the Study of Trabecular Bone Mechanics, Journal of Biomechanics, vol. 24, No. 9, pp. 825-839, 1991.
Simões, J.A.O., Taylor, M., et al., Preliminary investigation of a novel controlled stiffness proximal femoral prosthesis, Proceedings of the Institution of Mechanical Engineers, vol. 212, Part H, pp. 165-175, 1998.
Spector, M., Chapter 19: Low Modulus Porous Systems, Non-Cemented Total Hip Arthroplasty, edited by R. Fitzgerald, Raven Press, Ltd., New York, NY, pp. 227-241, 1988.
Lembert, E. Galante, J., Rostoker, W., Fixation of Skeletal Replacement by Fiber Metal Composites, Clinical Orthopaedics and Related Research, vol. 87, pp. 303-310, 1972.
Tensi, H.M., Gese, H., Ascherl, R., Non-linear three-dimensional finite element analysis of a cementless hip endoprosthesis, Proceedings of the Institution of Mechanical Engineers: Journal of Engineering in Medicine, vol. 203, Part H, pp. 215-222, 1989.
Mukherjee, D., Saha, S., The Application of New Composite Materials for Total Joint Arthroplasty, Journal of Long-Term Effects of Medical Implants, vol. 3, No. 2, pp. 131-141, 1993.
Ryan, G., Pandit, A., Apatsidis, D.P., Fabrication methods of porous metals for use in orthopaedic applications, Biomaterials, vol. 27, No. 13, pp. 2651-2670, 2006.
Li, C., Zhu, Z., Dynamic Young's modulus of open-porosity titanium measured by the electromagnetic acoustic resonance method, Journal of Porous Materials, vol. 13, pp. 21-26, 2006.
Ji, S., Gu, Q., Xia, B., Porosity dependence of mechanical properties of solid materials, Journal of Materials Science, vol. 41, pp. 1757-1769, 2006.
Wang, L. Tseng, K.K., A multi-scale framework for effective elastic properties of porous materials, Journal of Materials Science, vol. 38, pp. 3019-3027, 2003.
Ramakrishnan, N., Effective Elastic Moduli of Porous Ceramic Materials, Journal of the American Ceramic Society, vol. 76, No. 11, pp. 2745-2752, 1993.
O'Kelly, K.U., Carr, A.J., McCormack, B.A.O., Minimum solid area models applied to the prediction of Young's modulus for cancellous bone, Journal of Materials Science: Materials in Medicine, vol. 14, pp. 379-384, 2003.
Herakovich, C.T., Baxter, S.C., Influence of pore geometry on the effective response of porous media, Journal of Materials Science, vol. 34, No. 7, pp. 1595-1609, 1999.
Hashin, Z, The Elastic Moduli of Heterogeneous Materials, Journal of Applied Mechanics, vol. 29, pp. 143-150, 1962.
Rice, R,W., Microstructure Dependence of Mechanical Behavior of Ceramics, Treatise on Material Science, vol. 11, pp. 199-381, Academic Press, New York, 1977.
Boccaccini, A. R., Fabrication, Microstructural Characterization and Mechanical Properties of Glass Compacts Containing Controlled Porosity of Spheroidal Shape, Journal of Porous Materials, vol. 6, pp. 369-379, 1999.
Boccaccini, A.R., Comment on "Dependence of ceramic fracture properties on porosity", Journal of Materials Science Letters, vol. 13, pp. 1035-1037, 1994.
Rice, R.W., Evaluation and extension of physical property-porosity models based on minimum solid area, Journal of Materials Science, vol. 31, pp. 102-118, 1996.
Knudsen, F.P., Dependence of Mechanical Strength of Brittle Polycrystalline Specimens on Porosity and Grain Size, Journal of the American Ceramic Society, vol. 42, No. 8, pp. 376-387, 1959.
Roberts, A.P., Garboczi, E.J., Elastic Properties of Model Porous Ceramics, Journal of the American Ceramic Society, vol. 83, No. 12, pp. 3041-3048, 2000.
Roberts, A.P., Garboczi, E.J., Modeling the microstructure and elastic properties of complex materials, Proceedings of the Intenational Conference on Modeling and Simulation of Microsystems, Applied Computational Research Society, San Diego, California, Mar. 2000.

Ang, K.C., Leong, K.F., Chua, C.K., Investigation of the mechanical properties and porosity relationships in fused deposition modelling-fabricated porous structures, Rapid Prototyping Journal, vol. 12, No. 2, pp. 100-105, 2006.
Ganesh, V.K., Ramakrishna, K., Ghista, D.N., Biomechanics of bone-fracture fixation by stiffness-graded plates in comparison with stainless-steel plates, BioMedical Engineering OnLine, 4:46, 15 pgs., 2005.
Gerundini, M., Fusco, U., Avai, A., Maistrelli, G., Cementless R.M. Isoelastic Total Hip Prosthesis in Revision Surgery for Loose Prostheses, Italian Journal of Orthopaedics and Traumatology, vol. 13, No. 2, pp. 159-165, 1987.
Hollister, S.J., Maddox, R.D., Taboas, J.M., Optimal design and fabrication of scaffolds to mimic tissue properties and satidfy biological constraints, Biomaterials, vol. 23, pp. 4095-4103, 2002.
Hollister, S.J., Porous scaffold design for tissue engineering, Nature Materials, vol. 4, pp. 518-524, 2005.
Horne, G., Berry, N., Collins, D., Isoelastic Uncemented Hip Arthroplasty—Early Experience, Australian and New Zealand Journal of Surgery, vol. 57, pp. 461-466, 1987.
Howk, D., Chu, T-M., Design Variables for Mechanical Properties of Bone Tissue Scaffolds, Proceedings of the Rocky Mountain Bioengineering Symposium, pp. 278-283, Apr. 2006.
Hutmacher, D.W., Sittinger, M., V. Risbud, M.V., Scaffold-based tissue engineering: rationale for computer-aided design and solid free-form fabrication systems, TRENDS in Biotechnology, vol. 22 No. 7, pp. 354-362, 2004.
Krishna, B.V., Xue, W., Bose, S., Bandyopadhyay, A., Engineered Porous Metals for Implants, JOM (Journal of Metals), vol. 60, No. 5, pp. 45-48, 2008.
Krishna, B.V., Bose, S., Bandyopadhyay, A., Low stiffness porous Ti structures for load-bearing implants, Acta Biomaterialia, vol. 3, pp. 997-1006, 2007.
Leong, K.F., Cheah, C.M., Chua, C.K., Solid freeform fabrication of three-dimensional scaffolds for engineering replacement tissues and organs, Biomaterials, vol. 24, pp. 2363-2373, 2003.
Lin, C-Y., Wirtz, T., Lamarca, F., Hollister, S.J., Structural and mechanical evaluations of a topology optimized titanium interbody fusion cage fabricated by selective laser melting process, Journal of Biomedical Materials Research, vol. 83, No. 2, pp. 272-279, 2007.
Naing, M.W., Chua, C.K., Leong, K.F., Wang, Y., Fabrication of customised scaffolds using computer-aided design and rapid prototyping techniques, Rapid Prototyping Journal, vol. 11, No. 4, pp. 249-259, 2005.
Niinimaki, T., Puranen, J., Jalovaara, P., Total hip arthroplasty using isoelastic femoral stems, The Journal of Bone and Joint Surgery, vol. 76-B, No. 3, 1994.
Niinimaki, T., Puranen, J., Jalovaara, P., Revision arthroplasty with an isoelastic uncemented femoral stem, International Orthopaedics, vol. 19, pp. 298-303, 1995.
Niinimaki, T., Jalovaara, P., Bone loss from the proximal femur after arthroplasty with an isoelastic femoral stem, Acta orthopaedica Scandinavica, vol. 66, No. 4, pp. 347-351, 1995.
Ryan, G.E., Pandit, A.S., Apatsidis, D.P., Porous titanium scaffolds fabricated using a rapid prototyping and powder metallurgy technique, Biomaterials, vol. 29, pp. 3625-3635, 2008.
Ryan, G.E., McGarry, P., Pandit, A.S., Apatsidis, D.P., Analysis of the Mechanical Behavior of a Titanium Scaffold With a Repeating Unit-Cell Substructure, Journal of Biomedical Materials Research, vol. 90, No. 2, pp. 894-906, 2009.
Santos, E.C., Osakada, K., et al., Microstructure and mechanical properties of pure titanium models fabricated by selective laser melting, Proceedings of the Institution of Mechanical Engineers, vol. 218, No. 7, pp. 711-719, 2004.
Shimko, D.A., Shimko, V.F., Effect of Porosity on the Fluid Flow Characteristics and Mechanical Properties of Tantalum Scaffolds, Journal of Biomedical Materials Research, vol. 73, No. 2, pp. 315-324, 2005.
Simões, J.A., Vaz, M.A., The influence on strain shielding of material stiffness of press-fit femoral components, Proceedings of the Institution of Mechanical Engineers, vol. 216, No. 5, pp. 341-346, 2002.

(56) References Cited

OTHER PUBLICATIONS

Stahl, D., Gervasi, V., Design and Fabrication of Components with Optimized Composite Microstructures, Proceedinas of 2005 NSF DMII Grantees Conference, Scottsdale, Arizona.

Stahl, D., Gervasi, V., Design and Fabrication of Components with Optimized Composite Microstructures, Proceedings of 2006 NSF Design, Service, and Manufacturing Grantees and Research Conference, St. Louis, Missouri.

Sun, W., Starly, B., Nam., J., Darling, A., Bio-CAD modeling and its applications in computer-aided tissue engineering, Computer-Aided Design, vol. 37, pp. 1097-1114, 2005.

Sypeck, D.J., Parrish, P.A., Wadley, H., Novel hollow powder porous structures, Proceedings of Porous and Cellular Materials for Structural Applications Symposium held Apr. 1998, San Francisco, California.

Taboas, J.M., Maddox, R.D., Krebsbach, P.H., Hollister, S.J., Indirect solid free form fabrication of local and global porous, biomimetic and composite 3D polymer-ceramic scaffolds, Biomaterials, vol. 24, No. 1, pp. 181-194, 2003.

Xue, W.B., Krishna, B.V., Bandyopadhyay, A., Bose, S., Processing and biocompatibility evaluation of laser processed porous titanium, Acta Biomaterialia, vol. 3, pp. 1007-1018, 2007.

Zardiackas, L.D., Parsell, D.E., et. al., Structure, Metallurgy, and Mechanical Properties of a Porous Tantalum Foam, Journal of Biomedical Materials Research, vol. 58, No. 2, pp. 180-187, 2001.

Zein, I., Hutmacher, D.W., Tan, K.C., Teoh, S.H., Fused deposition modeling of novel scaffold architectures for tissue engineering applications, Biomaterials, vol. 23, No. 4, pp. 1169-1185, 2002.

Zimbeck, W.R., Rice, R.W., Freeform fabrication of components with designed cellular structure, Materials Research Society symposium proceedings, vol. 542, pp. 165-176, 1998.

Boccaccini, A.R., Fan, Z., A New Approach for the Young's Modulus-Porosity Correlation of Ceramic Materials, Ceramics International, vol. 23, pp. 239-245, 1997.

Cannillo, V., et. al., Use of numerical approaches to predict mechanical properties of brittle bodies containing controlled porosity, Journal of Materials Science, vol. 39, pp. 4335-4337, 2004.

Christie, M.J., Deboer, D.K., et. al., Primary Total Hip Use of the Modular S-ROM Prosthesis, The Journal of Bone and Joint Surgery, vol. 81-A, No. 12, pp. 1707-1716, 1999.

Karageorgiou, V., Kaplan, D., Porosity of 3D biomaterial scaffolds and osteogenesis, Biomaterials, vol. 26, pp. 5474-5491, 2005.

Li, H., Oppenheimer, S.M., et. al., Effects of Pore Morphology and Bone Ingrowth on Mechanical Properties of Microporous Titanium as an Orthopaedic Implant Material, Japanese Materials Transactions, vol. 45, No. 4, pp. 1124-1131, 2004.

Li, X., Wang, C-T., Zhang, W-G., Li, Y-C., Properties of a porous Ti—6Al—4V implant with a low stiffness for biomedical application, Proceedings of the Institution of Mechanical Engineers, vol. 223, pp. 173-178, 2009.

Rehme, O., Schwarze, D., Emmelmann, C., Selective laser melting of customized implants with cellular surface structures for optimized elasticity and improved osseointegration, Proceedings of RPD2006 Moulds Events Conference, Marinha Grande, Portugal, Nov. 2006.

Segurado, J., Llorca, J., A numerical approximation to the elastic properties of sphere-reinforced composites, Journal of the Mechanics and Physics of Solids, vol. 50, pp. 2107-2121, 2002.

Shen, H., Oppenheimer, S.M., Durand, D.C., Brinson, L.C., Numerical modeling of pore size and distribution in foamed titanium, Mechanics of Materials, vol. 33, pp. 933-944, 2006.

Shen, H., Brinson, L.C., Finite element modeling of porous titanium, International Journal of Solids and Structures, vol. 44, pp. 320-335, 2007.

Shen, H., Brinson, L.C., A numerical investigation of the effect of boundary conditions and representative volume size for porous titanium, Journal of Mechanics of Materials and Structures, vol. 1, No. 7, pp. 1179-1204, 2006.

Spoerke, E.D., Murray, N.G., et al., A bioactive titanium foam scaffold for bone repair, Acta Biomaterialia, vol. 1, No. 5, pp. 523-533, 2005.

Spoerke, E.D., Murray, N.G., et al., Titanium with aligned, elongated pores for orthopedic tissue engineering applications, Journal of Biomedical Materials Research, vol. 84, No. 2, pp. 402-412, 2008.

Thelen, S., Barthelat, F., Brinson, L.C., Mechanics considerations for rnicroporous titanium as anorthopedic implant material, Journal of Biomedical Materials Research, vol. 69, No. 4, pp. 601-610, 2004.

Van Cleynenbreugel, T., et al., Trabecular bone scaffolding using a biomimetic approach, Journal of Materials Science, vol. 13, pp. 1245-1249, 2002.

Wen, C.E., Yamada, Y., et al., Porous Bioresorbable Magnesium as a Bone Substitute, Materials Science Forum, vols. 419-422, pp. 1001-1006, 2003.

Hollister, S.J., Levy, R.A., et al., An image-based approach for designing and manufacturing craniofacial scaffolds, International Journal of Oral and Maxillofacial Surgery, vol. 29, pp. 67-71, 2000.

Lin, C-Y., Hisiao, C-C., et al., Interbody Fusion Cage Design Using Integrated Global Layout and Local Microstructure Topology Optimization, SPINE, vol. 29, No. 16, pp. 1747-1754, 2004.

Lin, Y.L., Kikuchi, N., Hollister, S.J., A novel method for biomaterial scaffold internal architesture desion to match bone elastic properties with desired porosity, Journal of Biomechanics, vol. 37, pp. 623-636, 2004.

Vendra, L. Rabid, A., Evaluation of modulus of elasticity of composite metal foams by experimental and numerical techniques, Materials Science and Engineering A, vol. 527, pp. 1784-1790, 2010.

* cited by examiner

Holes for implant fixation and bone ingrowth

ORTHOPAEDIC IMPLANTS AND METHODS OF FORMING IMPLANT STRUCTURES

RELATED APPLICATION

This application claims the benefit of co-pending U.S. Provisional Patent Application No. 61/436,459, filed 26 Jan. 2011.

BACKGROUND OF THE INVENTION

Joint replacement surgery has been performed to relieve pain and restore joint function for more than 50 years and has become a relatively common procedure. These procedures typically involve lower extremity joints. The most recent data from the CDC's National Center for Health Statistics summarizes that 230,000 hip replacement and 540,000 knee replacement surgeries were performed in the U.S. in 2007 alone. The success of these surgeries is dependent upon the use of biocompatible materials, satisfactory design of the endoprosthesis or implant itself and proper operative techniques.

Design of the implant is complicated by the large bending stiffness (or flexural rigidity) of orthopaedic implants which is at least 10 times greater than cortical bone. Effects of this stiffness mismatch have been extensively studied relative to total hip arthroplasty (THA) and clinical experience has shown that stiffness mismatch is the primary cause of accelerated bone resorption due to stress shielding. This response to sub-optimal bone loading can lead to loss of proximal support, implant subsidence, potential bone fracture, possible fatigue fracture of the implant, and, most importantly, reduction of bone stock that jeopardizes the outcome of any future revision surgery.

Despite widespread awareness of these factors, the problem of implant stiffness has not been completely solved. Research suggests that flexural rigidity should vary along the length of the prosthesis using "anisotropic" materials with a defined structure to allow a "distribution of elastic properties inside the stem" or within the bounding geometry of other implant configurations.

Past attempts to incorporate design features that reduce flexural rigidity have yielded inconsistent results or failures due to biomaterial incompatibilities and practical manufacturing complications. Recent developments in additive manufacturing (AM) processes allow the production of closed-cell porous microstructures in titanium, cobalt-chromium or other metals as a practical means of implant fabrication.

Given the clinical concerns relative to bone loss due to the stiffness mismatch between bone and implant, the use of closed-cell porosity to modify the effective moduli of an implant, and recent developments in practical AM technology, this invention applies engineered porosity to predictably reduce the flexural rigidity of an orthopaedic implant.

While research efforts have focused on the clinical problems associated with total hip arthroplasty (THA), similar problems exist with other orthopaedic implants. Early failures of acrylic and nylon prostheses in THA created an impetus for the development and use of metal components. However, problems associated with implant loosening along with proximal and distal migration tempered early enthusiasm for these designs. Due in part to these issues, THA procedures, pioneered by Charnley in 1958, came to rely on acrylic bone cement for intramedullary fixation. The popularity of the Charnley technique was due to its high rate of success in older patients. However, a lower success rate became evident in younger patients, usually under age 40. Over the intervening years, painful loosening of the implant became more common. By 1983, a National Institutes of Health consensus panel on THA named loosening as the number one problem with cemented prostheses. The loosening of these cemented implants was frequently accompanied by severe osteolysis which complicated subsequent revision surgeries.

In response to these problems, press-fit cementless fixation, which relies on a larger, canal-filling geometry, was developed for use with young and active patients. One disadvantage of this increase in implant size is a larger mismatch in stiffness between the implant and the adjacent bone than would be typical of stems that rely on cement for fixation.

Prior to the surgical insertion of the prosthesis, the hip joint load is carried directly by the bone, with loads applied to the head of the femur and forces distributed across the entire cross section of the femoral shaft. This loading leads to a homeostatic equilibrium in which the amount of stress-induced bone formation is balanced by the amount of bone loss associated with normal osteoclast activity. Bending and axial compression are the major modes of femoral loading prior to THA. After insertion, the load is transferred from the endoprosthesis to the bone through localized contact with the metaphysis and medullary cavity and as shear across the bone/prosthesis interface.

In conceptual terms, the femur is a hollow tube that, due to its offset geometry, undergoes bending in response to ambulatory loads. Filling this hollow tube with a metal prosthesis stiffens the tube and accordingly reduces its ability to bend in response to the applied load. As a result, the stresses in the cortical bone adjacent to the endoprosthesis are subnormal and the bone reacts with a reduction in cortical thickness. This is a natural process of strain-adaptive bone remodeling which, presumably, leads to a new equilibrium state.

Research using dual energy X-ray absorptiometry (DEXA) indicates that a new state of equilibrium is not achieved and that bone loss, while diminished, is progressive over time. The reduction in the physiologic load seen by the proximal bone results in a mechanically-induced osteopenia, generally referred to as "stress shielding". There is no standard testing protocol, nor a consistent definition of this phenomenon.

Stress shielding refers to a reduction in the stress levels within the periprosthetic bone and cannot be perceived per se. The mechanical parameters that regulate periprosthetic bone loss are difficult to quantify. However, it is widely accepted that the greater the flexural rigidity of the implanted stem, the greater the extent of stress shielding in the proximal femur. This phenomenon, particularly in the case of relatively stiff stems, can cause bone mass reductions up to 50%.

A concern with THA prostheses is the possibility that resorptive bone remodeling will, in the long term, lead to loss of proximal implant support, implant subsistence and implant or bony fracture. Research on local stresses and bone adaptation by Huiskes et al. indicates that the most severe complication associated with joint replacement is aseptic loosening. This threatens the long-term structural integrity of the bone-prosthesis structure and the application of THA to younger (<55 years) patients.

Using dual-energy X-ray absorptiometry (DEXA) to assess bone loss, Kilgus et al. reported a 35% reduction in bone mineral density in the area adjacent to the proximal third of the prosthesis after 5-7 years. In a subsequent study of periprosthetic bone remodeling, Sychterz et al. reported that after ~6 years following THA, DEXA analyses disclosed an average 23% overall decrease in bone mineral content in the femur implanted with an prosthesis and that females experienced an average bone loss of 31%, significantly higher than the 12% average loss in males.

Studies by Lewis et al. on the influence of prosthetic stem rigidity suggest that the loss of proximal support due to bone resorption, with firm fixation distally, may also be a major cause of fatigue failure of femoral stems. Engh et al. demonstrated that after an average of 5 years, the bone loss associated with cementless THA ranged from 7 to 52%, with the greatest loss in the femoral metaphysis proximal to the lesser trochanter. In a later study, Engh et al. confirmed that adjacent to the proximal third of the prosthesis the extent of proximal bone loss was substantial and ranged from 27 to 78%.

Glassman et al. conclude that the loss of supportive bone may predispose patients to progressive implant migration in the absence of loosening. Thus, whether the clinical concern is initial fixation, loosening, subsidence, or stem fracture, the bone loss due to stress shielding impairs the construction as a whole and can lead to inadequate support for a revision implant in the future.

Adaptive bone reactions around prostheses have been reported to stabilize after approximately a year post-operatively, but progressive late reactions have also been noted by others. Kiratli et al. evaluated post-operative bone loss using DEXA and concluded that bone remodeling does not stabilize in two years. Rather, there is evidence of continued resorption between 2 and 5 years post-surgery and that bone loss progresses in small decrements not discernible by standard radiographs. Other assessments of bone loss over time are often inconclusive as early clinical studies of bone resorption relied on radiographic measurements that predated DEXA technology.

Despite these data accuracy concerns, the study by Huiskes et al. on stress shielding and bone resorption notes that even if the bone remodeling process does stop after a few years, a loss of proximal bone mass on the order of 50% "provides little confidence for the time when these patients get older and become prone to falls and other accidents as . . . the remaining bone may not be adequate to withstand the impact forces". As Huiskes noted in two subsequent studies on THA complications, that while " . . . the stress shielding scenario constitutes a potential failure mechanism", clinical failures are "hardly ever reported". However, research indicates that the loss of proximal support increases the risk of fatigue fracture of the stem and jeopardizes any future revision that would require extraction of an otherwise well-fixed stem. Surgery of this type is a technically challenging procedure that may not leave adequate bone for satisfactory support of a revision implant. Studies by Huiskes et al., Nistor et al., Bugbee et al. and Weinans et al. over 11 years have summarized that periprosthetic bone remodeling may contribute to increased midthigh pain or decreased function, fracture of the femur or the femoral component, loss of fixation of the implant, increased prevalence or severity of osteolysis and, again, difficulty in performing a revision. This is especially significant when considering that cementless implants are typically used in younger patients where the potential for revision during the patient's lifetime is high and the need to keep reconstructive options open is paramount.

Another concern regarding cementless femoral hip stems is persistent thigh pain despite stable fixation. Significant thigh pain after implantation of a cementless prosthesis occurs in as many as 20% of arthroplasty patients, a problematic outcome as one of the clinical indications for performing THA in the first place is joint pain. Although the etiology of thigh pain is unclear, research suggests that it is attributable to excessive stem stiffness and the resulting modulus mismatch between implant and host bone. These results indicate that clinical concerns regarding excessive stem stiffness extend beyond proximal bone loss.

Over the past 30 years, various implant features have been proposed as factors contributing to subsequent stress shielding. Among these are stem stiffness, implant geometry, stem material, ingrowth surface, and level of porous coating. Canine studies have demonstrated that an effective means of promoting proximal load transfer and a reduction in stress shielding is to reduce the stiffness of the stem. Additionally, Sumner et al. noted that other variables, including the presence, absence or placement of the porous coating, did not significantly affect the pattern of long-term bone remodeling.

The indication that stem stiffness, rather than porous coating level, plays a dominant role in affecting bone resorption was also confirmed in human studies. Bobyn et al. determined that the long-term femoral strain patterns can be substantially altered by a 3- to 5-fold reduction in stem stiffness and that the greatest effect could be realized in the femoral shaft adjacent to the middle one-half of the stem.

Work by Engh et al. on the influence of stem size noted that the incidence of pronounced bone resorption occurs in at least 20% of cases and increases with stem size and the flexural rigidity of the implant. In their study of 411 cases of cementless THA, stems≥13.5 mm in diameter showed 5 times the incidence of pronounced resorption as compared with stems≤12.0 mm in diameter. Bobyn et al. concluded that to reduce bone resorption, the implant should possess a bending stiffness of about one-half to one-third that of the host femur.

Dujovne et al. presented data on the axial and bending stiffness of 65 femora calculated from cross-sectional CT scans taken at 10 mm intervals along the longitudinal axis of each femur. These data were compared to that of two commercially-available implant designs. Dujovne et al. note that while the commercial implants were as much as 2 times less stiff than the femur in the distal region, these same implants were 4 to 5 times stiffer than the bone in the proximal region. In an evaluation of a hollow prosthesis, Gross et al. emphasized the goal of "stiffness adjustment" by noting that the proximal 10 mm of the bone is most sensitive to changes in stem rigidity and could benefit most from an "optimization process". Bobyn et al. also observed that proximal bone resorption would be attenuated if the stiffness of the proximal stem could be "appropriately adjusted" relative to that of the metaphysis. Dujovne et al. add that while "mechanical compatibility" cannot be quantified, there needs to be some acceptable mechanical relationship between implant and femur in terms of stiffness parameters.

Early attempts to incorporate design features that reduce the flexural rigidity of the implant and minimize bone resorption due to stress shielding have led to inconsistent results and, in some cases, catastrophic failures. Researchers and implant manufacturers have developed, marketed and evaluated reduced-stiffness implants broadly characterized as "isoelastic" prostheses. Most of these isoelastic designs have involved changing material properties or modifying the structural characteristics to reduce the moment of inertia of the implant.

Studies by Morscher et al. suggested that "by adjusting the physical characteristics of the foreign material to that of the bone tissue" they achieved an "optimum approximation of the physical characteristics of an implant to that of bone". As described by Andrew et al., " . . . the concept of isoelasticity is that the implant and bone should deform as one unit. To achieve this, the stiffness of the cortical tube, and the femoral stem it surrounds, must be approximately matched, reducing relative movement between the bone and the femoral stem". While this perspective may have conceptual appeal, neither of these studies defined elasticity or stiffness in quantifiable terms.

The RM Isoelastic® stem (Mathys Ltd. Bettlach, Switzerland) was introduced in 1973 as one of the first commercial efforts aimed at achieving a more physiological loading of the femur. Polyacetyl resin was selected for the bulk of the femoral component because of its "tensile strength, durability and the proximity of its modulus to that of bone" with a stainless steel core to avoid "over-elasticity" in the neck region of the prosthesis. An early evaluation by Morscher et al. of the RM Isoelastic (RMI) implant focused on testing done to assure biocompatibility but offers little quantitative data regarding the stiffness of the implant. As noted in a subsequent report by Morscher et al., because of the high incidence of loosening of the RMI implant, "reinforcement" of the prosthesis became necessary in 1977. Although no data were presented, these authors maintain that "much better results were obtained" as a consequence of this modification.

Initial clinical experience with the RMI implant was described by Bombelli et al. but provided little detail other than to note that " . . . we have tested the fracture strength of the collar-neck portion experimentally and shown it to be double that of a steel prosthesis and four to five times greater than the strength of the bone itself. The plastic-metal combination is a little more elastic than pure metal . . . to allow for a certain amount of shock absorption".

The DEXA-based evaluation by Ang et al. summarizes the encouraging short-term≤(1 year) results of the RMI stem and notes that loss of bone mass was "minor, recovering early, in the flexible isoelastic implants". However, earlier assessments which lacked the accuracy of DEXA technology concluded that "while early results are encouraging, this prosthesis needs a longer follow-up evaluation to prove its effectiveness". In a 7-9 year follow-up study, Niinimaki et al. acknowledged that while early results were encouraging, the RMI stem shows a high rate of loosening and the results are "worse than those reported for other uncemented stems". Matricali et al. also evaluated the RMI prosthesis in 19 revision surgeries and reported that they had a "far less acceptable result" than that reported by others.

In a more recent report, Ali et al. conclude that "we have concerns over the longer term survival of the [RMI] prosthesis" due to its high incidence of lateral migration. In the longest study of the RMI implant, Trebse et al. state that with a survival rate of 69% (10-year) and 48% (15-year), "it presents one of the worst performances reported for a cementless total hip replacement". FIG. 1 provides visual indication of extent of the longer-term problems associated with the RMI implant.

As a result of sub-standard clinical experience, the concept of isoelasticity became an example of failed innovation as described by Huiskes. In another evaluation of the RMI prosthesis, Au noted that the perceived advantage of isoelasticity "is hard to justify in clinical practice". The clinical review of this prosthesis by Jakim et al. concluded that the concept of isoelasticity has failed to fulfill original clinical expectations and that "it seems unlikely that an ideal mimic can be fashioned from plastic materials".

Several researchers evaluated or promoted the adoption of a hollow-stemmed prosthesis as a means of achieving a more nearly "physioelastic" condition. The hollow Cenos (Artos Medizinische Produkte GmbH, Berlin, Germany) stem relies on extra flexibility to reduce stress shielding with "very satisfying" but unquantified results reported by Schmidt et al. after 1 year of clinical experience. Viceonti et al. and Engelhardt et al. have also evaluated implant properties and stress distribution in the femur as a result of incorporating transverse holes or removing material from the proximal one-third of the stem. Effects of these modifications were inconclusive and influenced by other design or manufacturing issues. Another hollow stem, the SHEP implant (Howmedica GmbH, Schönkirchen, Germany) as described by Täger and shown in FIG. 2, has holes along the length of the cobalt-chromium (CoCr) alloy stem and relies on the ingrowth of cancellous bone to fixate the implant. Täger reports a 94% success rate for the use of the SHEP stem in at least 150 patients over a six-year period.

Butel developed and evaluated a nonrigid femoral implant that claimed to provide a unit comprised of bone and prosthesis that in combination would have similar elastic properties as bone. The Butel stem consisted of four metallic rods, joined at the distal end. In a review of 61 hips using this stem, Butel et al. do not include any quantitative analysis of the stem design or its effect on bone resorption. A subsequent clinical evaluation by Jacobsson et al. noted that the flexible stem of the Butel femoral component produces high shear forces in the proximal interface which has led to loosening, overload on the prosthesis and fatigue fracture. With a failure rate of 43%, the Butel femoral prostheses were deemed a "clinical failure".

Another approach to the reduction of stem stiffness is inclusion of a slot in the distal stem, as in the S-ROM® stem (Joint Medical Products, Stamford, Conn.) as shown in FIG. 3. Cameron evaluated the clinical performance of this stem, which is split distally to reduce bending stiffness. While a 3-6 year evaluation disclosed acceptable overall results and a significant reduction in thigh pain, the effect of the slotted distal stem design does not address proximal implant stiffness, the zone in which the greatest mismatch in rigidity occurs.

Other methods of reducing femoral implant stiffness include the removal of metal from the outer surface of the component and replacement with a polymer to fill out the geometry of the prosthesis. Clinical trials by Nistor et al. of the LMPCH titanium stem (Biomet, Inc., Warsaw, Ind.) layered with solid and porous polyethylene were generally not successful due to implant subsidence. High rates of revision, mechanical failure (delamination) of the polymer coating and associated osteolysis led to the abandonment of the design.

Another composite material prosthesis is the Epoch® hip (Zimmer, Inc., Warsaw, Ind.). This current femoral stem design incorporates an inner metallic core, an outer porous metal mesh of titanium (Ti) metal fibers with effective thickness of 0.83 mm and an intervening polymer layer of polyaryletherketone that has been injection-molded onto the CoCr core. The clinical report by Akhavan et al. noted that the proximal bending stiffness of the implant is "similar" to that of the proximal part of the femur and two to six times less than the bending stiffness of a comparatively sized Ti or CoCr alloy implant. The clinical study of the Epoch stem by Glassman et al., showed stable initial fixation and minimal micromotion but the study was "too short to determine the long-term outcome of the procedure" relative to adaptive bone remodeling. Longer-term studies by Karrholm et al. noted that proximal bone resorption was less than with other uncemented stems.

After reporting on the poor clinical results of the RMI stem, Niinimaki et al. noted that " . . . the modulus of elasticity of the stem should perhaps be adjusted more accurately". Conclusions reached by Kuiper et al. and Simões et al. are similar, suggesting that the modulus of elasticity should vary along the prosthesis length, with a relatively high proximal-medial modulus and a low distal modulus, matching the cortical bone modulus at the prosthesis tip. The finite element (FE) studies of a controlled-modulus prosthesis by Simões et al. demonstrate that the desired load transfer distribution can be produced, minimizing both calcar stress shielding and interface micromotion. In a 2000 paper by Simões et al., the authors note that the development of a controlled-stiffness implant is limited by currently available materials and the fabrication process involved. "At present, for the hip prosthesis, this remains a theoretical solution since it is difficult to manufacture a device with a very highly differentiated modulus". Bobyn et al. concluded that only with the use of composite structures might it be possible to adequately address the stiffness mismatch for all stem sizes, especially in the metaphysis. Glassman et al. and Harvey et al. also recognized the potential advantage of carbon fiber composites which offer a combination of high fatigue strength and elastic moduli closer to bone than that of metal alloys. These composite materials can be fabricated to be nonhomogeneous and nonisotropic such that the flexural rigidity can be varied within different implant regions. Despite these perceived advantages, the clinical success of carbon fiber composite femoral implants has been limited by problems with stem fracture and inadequate fixation at the polymer-bone interface. These composite implants lack the ability for osseointegration as they cannot be fabricated with conventional porous coatings or other bone ingrowth surfaces. This practical complication leads research and development back to the use of metal alloys for an endoprosthesis.

Metallic implants continue to offer distinct advantages, including a proven history of use and FDA approval considerations. Although implant manufacturers have long promoted the use of titanium alloy stems as a "less stiff" material, adequate consideration of the consequences of stem geometry has been lacking. Glassman et al. noted that the flexural advantage of using Ti is reduced with the larger stem sizes (>14 or 15 mm diameter) because of the dominant effect of stem geometry on stiffness. However, even with smaller stem sizes, the proximal femur is still understressed by at least 10-fold with a Ti implant when compared to the stresses in the intact femur.

In 1972, Lembert et al. noted that if a prosthesis were made of a metallic material that was more compliant than solid metal, the "loads would be more evenly distributed and much, if not all, of the motion between the implant and bone would be overcome". While this predates recent concerns regarding micromotion at the bone-implant interface, some implant designs have incorporated structural design features which (either intentionally or as a result of unrelated requirements) have reduced the stiffness of the implant. For example, Bobyn et al. observed that the flutes on the distal portion of the HG Multilock (Zimmer, Inc.) stem, which increase in depth with increasing stem size, provide an additional gain in flexibility of up to 25% with the larger stem sizes as compared to that of a solid, non-fluted stem.

In an analysis of a cementless prosthesis, Tensi et al. note that neither a very stiff implant nor an "isoelastic" one provides an ideal solution. "Probably anisotropic materials, such as unidirectional solidified metal alloys, are a possible solution". Kuiper et al. in their study of the mathematical optimization of elastic properties arrived at a similar conclusion. "Reducing the stem stiffness decreases the amount of stress shielding and hence the amount of bone loss. However, this measure inevitably promotes higher proximal interface stresses and thereby increases the risk of proximal interface failure. The designer's task therefore is to optimize the stem stiffness in order to find the best compromise in the conflict. Yet, a better compromise might be found when the stem material was nonhomogeneous, in other words, when an arbitrary distribution of the elastic properties inside the stem was allowed". Mukherjee et al. suggested " . . . a material optimization scheme via finite element with input of the right material properties and a technology to fabricate devices which will allow the devices to have different strength and modulus properties from the proximal to the distal end".

The success of prior efforts to implement this scheme has been limited by combination of biomaterial incompatibilities, practical manufacturing complications and insufficient understanding of flexural rigidity as it is applied to orthopaedic implants. With the recent development of additive manufacturing processes, including the laser sintering and electron beam melting of biocompatible metallic powders, comes the potential to create closed cell porous materials as a practical means of reducing stem stiffness and tailoring the mechanical properties of the implant to clinical requirements.

Ryan et al. noted that while the use of titanium (Ti) in implants reduces the extent of stress shielding as compared to that of cobalt-chromium (CoCr), the stiffness mismatch is still substantial. To overcome this mismatch, Ryan et al. suggest the use of porous materials in implants. Their work and that of Li et al. note that mechanical properties of porous materials can be altered and optimized by controlling pore size and shape as well as pore distribution. This is a useful perspective as long as relationships between the porous structure and the resulting mechanical properties are known.

Because of their mechanical properties and established biocompatibility, the orthopaedic applications of porous metals have been mainly associated with the development of bone ingrowth surfaces on solid implants. This has led to the majority of research interest to be drawn to the development of open-cell porous metals although arguably greater potential lies with the use of closed-cell porous metals. "In such cases, bone ingrowth would not be the major interest, but rather the reduction in material stiffness that has been linked to early loosening following processes of bone loss due to stress shielding".

As it is time- and cost-prohibitive to determine the effective mechanical properties of each porous material experimentally, numerous mathematical relationships have been proposed to describe the dependence of mechanical properties on porosity. The physical meaning of these relationships is often unclear as most theoretical models are based on some idealized physical microstructure (e.g., uniform cubic, cylindrical or spherical pores arranged in a cubic array), and the resulting correlations often cannot be extended to real materials and potential clinical applications.

The majority of the theoretical equations for moduli have been derived by treating a representative volume of a porous solid as a special case of two-phase materials, evaluating them mathematically or empirically, and extending the conclusions to the continuum material. In a comparative review of these equations, Ramakrishnan noted that all of these methods involve two steps: to establish the stress and strain distributions for a simple two-phase geometry and then to modify the distributions, taking into account the interaction between the inclusion phases.

O'Kelly et al. characterize these theoretical methods into three main approaches: composite theory, cellular solids and minimum solid area (MSA). "The first approach assumes a two-phase material, with one phase having zero stiffness; the latter two assume a single phase permeated with voids". Herakovich et al. take a broader view and observe that there are two fundamentally different approaches to the study of porous media: those of the mechanics community and those of the materials community. The mechanics community has tended to consider a specific shape pore (often spherical) and then develop analytical solutions for mechanical properties as a function of pore volume fraction. In contrast, the materials community has tended to obtain experimental results for mechanical properties as a function of porosity and then find the "best-fit" curve where the parameters are associated with the pore geometry or method of fabrication. These different approaches yield divergent results and, in certain instances, formulas which are sometimes in direct contradiction. While the literature abounds with references to different porosity models and their appropriateness for a given set of conditions, the problem is that the microstructure corresponding to a particular formula is not precisely known. Thus, agreement or disagreement with data can neither confirm nor reject a particular model. Roberts and Garboczi note that the elastic properties of two-phase (solid-pore) porous materials depend on the geometrical nature of the pore space and solid phase as well as the value of porosity. Relevant aspects of porous materials may include pore shape and size, as well as the size and type of the interconnections between solid regions.

Despite different perspectives, researchers involved in the study of mechanical properties of porous materials do agree on two issues: that optimizing the overall mechanical properties of materials can be done through introducing different volume fractions and/or different shapes of pores into solids. However, despite the extensive body of research represented by existing porosity-property relationships, most lack predictive ability. Rice is critical of much of the prior work as "few investigators studying the dependence of elastic properties on porosity present anything more than density, i.e., average porosity data" when pore shape anisotropy can significantly alter these relationships and invalidate the results. Boccaccini added that most experimental studies in the open literature dealing with porous materials do not supply accurate quantitative descriptions of the porosity structure and cannot be considered for rigorous verification of theoretical approaches. In 1994, he further summarized the broader situation: The utility of a microstructure-property correlation is directly related to its ability to predict the property from microstructural measurements and thus to be used for design purposes.

The need to proactively address the concerns of stress shielding and the resulting bone resorption requires the use of validated methodology for predicting Young's modulus and Poisson's ratio of a regular porous structure, incorporating that structure in the implant and fabricating the resulting design. While these observations focused on bone resorption associated with stress shielding and THA, these concerns are equally valid for other orthopaedic implants.

In a 1996 paper on physical property-porosity models, Rice notes that the use of spherical particles or pores in the three basic close packings (cubic, orthorhombic and rhombohedral) has not been adequately evaluated and "isotropy has apparently not been considered before" as the presumption is that the mechanical properties of porous structures are isotropic. He further adds that Knudsen's original calculations as detailed in his 1959 paper, one of few describing the effect of defined porosity on mechanical properties, were of three different sphere stackings, but only for one [loading] direction for each of these [pore] stackings".

SUMMARY OF THE INVENTION

A porous material with a microstructure (here defined as feature size ranging from a radius of approximately 100 µm to 2000 µm), and methods of making the same, are disclosed that are tailored for a specific application and modify the structure to obtain the best possible combination of macroscopic properties. For optimization, the methodology preferably allows for manipulation of the porosity structures and the production of pores of well defined shapes. The resulting materials with "designed" porosity are useful as model systems to verify the accuracy of theoretical and numerical approaches that claim to describe the properties of porous materials and their use in implant structures.

It is an objective of the present invention to produce, using engineered porosity, a predictable modification of the effective moduli, specifically Young's modulus and Poisson's ratio, of an orthopaedic implant. A series of representative volume elements (RVEs) incorporating five possible regular arrangements of spherical porosity within a physical construct is disclosed. Four regular arrangements of spherical porosity are defined by cubic, orthorhombic and rhombohedral ordering of close-packed pores. The orientation of these RVE constructs can be changed to produce different mechanical properties in response to applied load. Factors such as pore size, separation distance and/or stacking arrangement can be varied to lead to a predictable modification in the effective moduli of the resulting construct.

Based on user preference, an implant segment having desirable biomechanical properties such as, but not limited to, effective moduli approached that of cortical bone, can be designed to provide for appropriate values of bending stiffness or flexural rigidity of this implant design.

Commercially available additive manufacturing (also referred to as rapid prototyping) processes including, but not limited to, selective laser melting (SLM), direct metal laser sintering (DMLS), laser engineered net shaping (LENS) and/or electron beam melting (EBM), can then be used for the production of the implant components.

The fundamental premise of this invention is that these additive (or rapid prototyping) processes can provide the technological platform for precise pore design and positioning for the production of clinically-relevant microstructures with improved mechanical properties appropriate for orthopaedic implant applications.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

The invention results from the response of series of representative volume elements (RVEs) under differing loading scenarios given regular (non-random) arrangements of spherical pores and the subsequent creation of unit cells (Boolean inverse) that result from those pore arrangements.

Regular close-packed arrangements, characterized by pores that are in contact with all adjacent pores at maximum porosity, are generated from the stacking and subsequent realignment of consecutive layers that incorporate rows of individual spherical pores. An additional non-close-packed pore model, the body-centered cubic (BCC) arrangement is disclosed.

Figure 1:
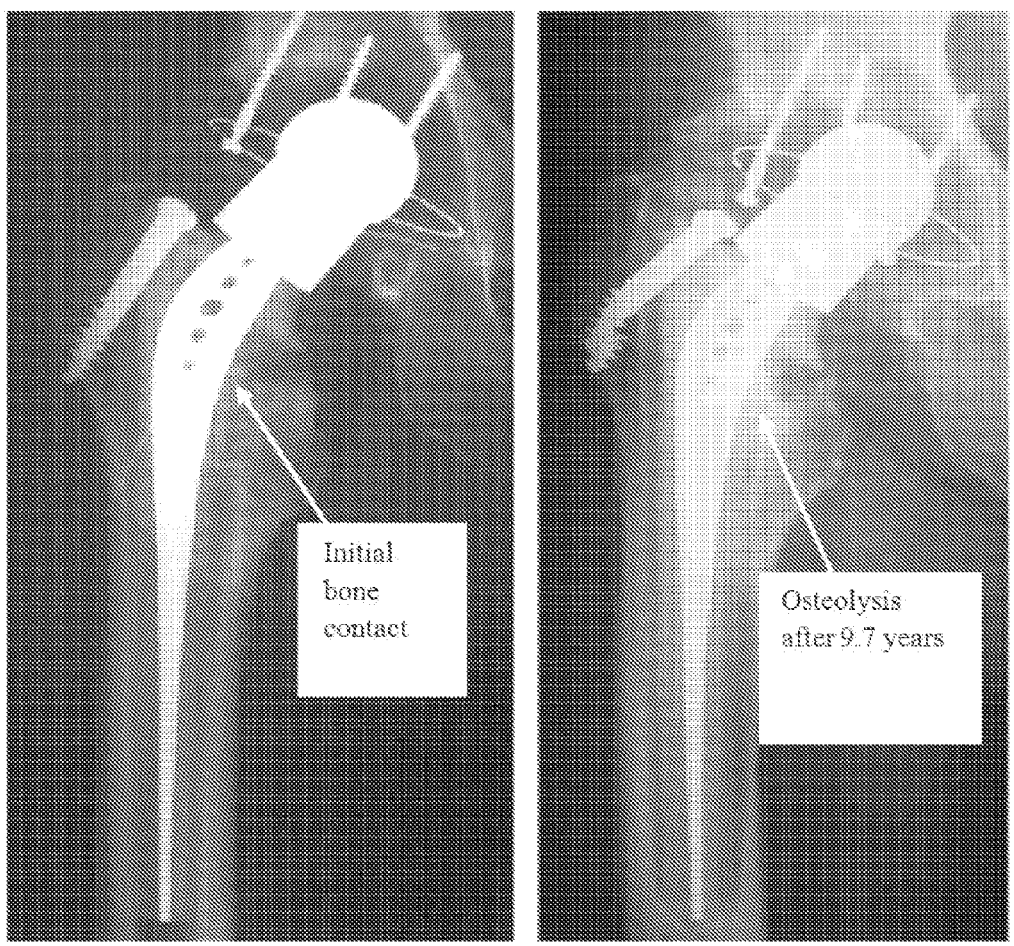
FIG. 1 is an image of the RM Isoelastic (RMI) implant, showing initial bone contact and osteolysis after roughly 10 years.
Figure 2:
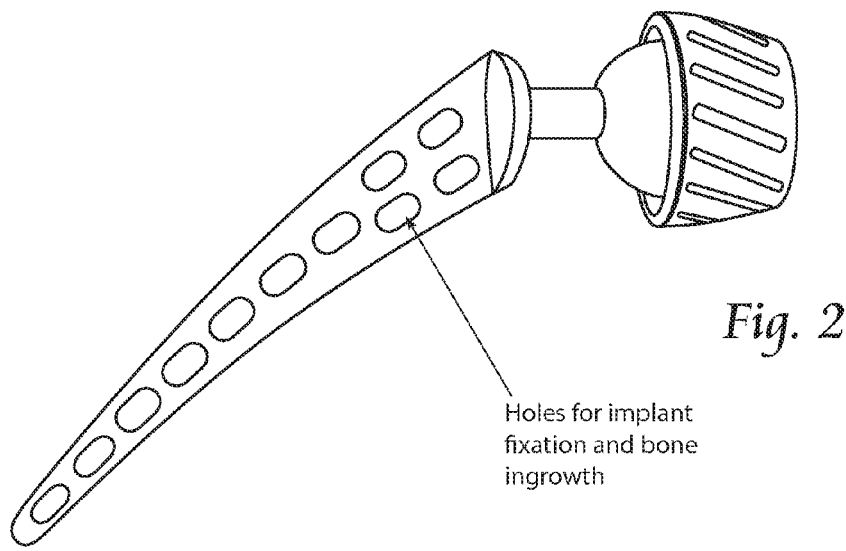
FIG. 2 is an image of the hollow Spongiosa-Hip joint-Endo-Prosthesis (SHEP)
Figure 3:
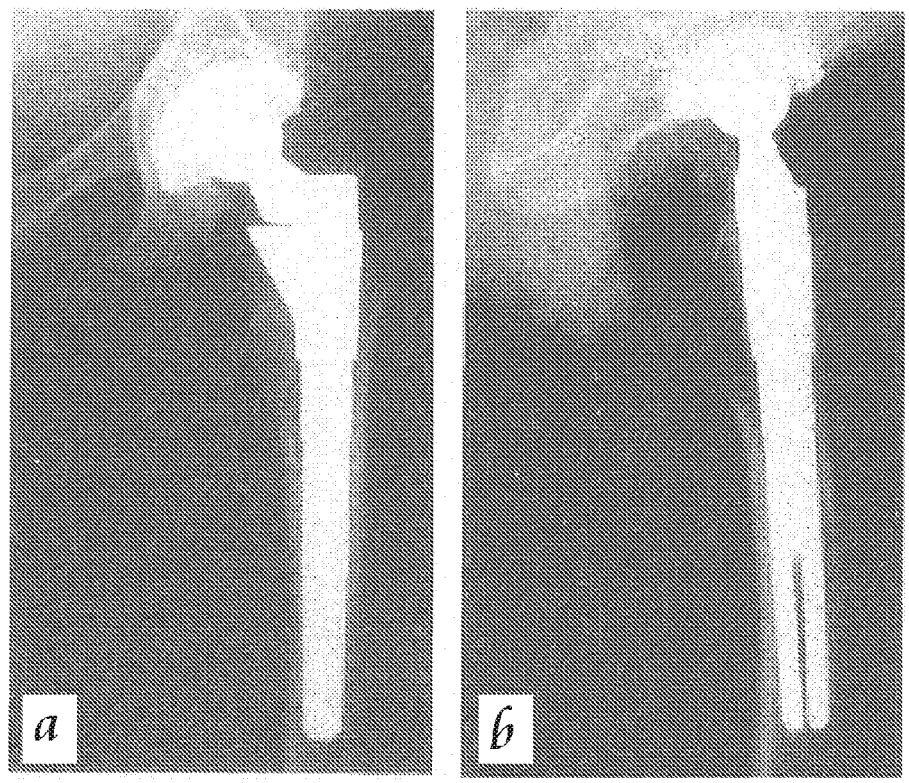
FIGS. 3a and 3b are images of the S-ROM prosthesis in a coronal plane and a sagittal plane, respectively.
Figure 4:
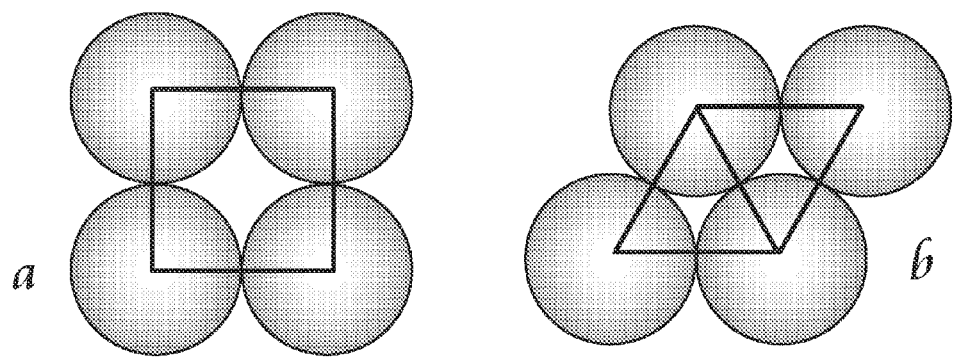
FIGS. 4a and 4b are side views of fundamental arrangements of porous layers for a square layer (90 deg) and a rhombic or triangular layer (60 deg), respectively.
Figure 5:
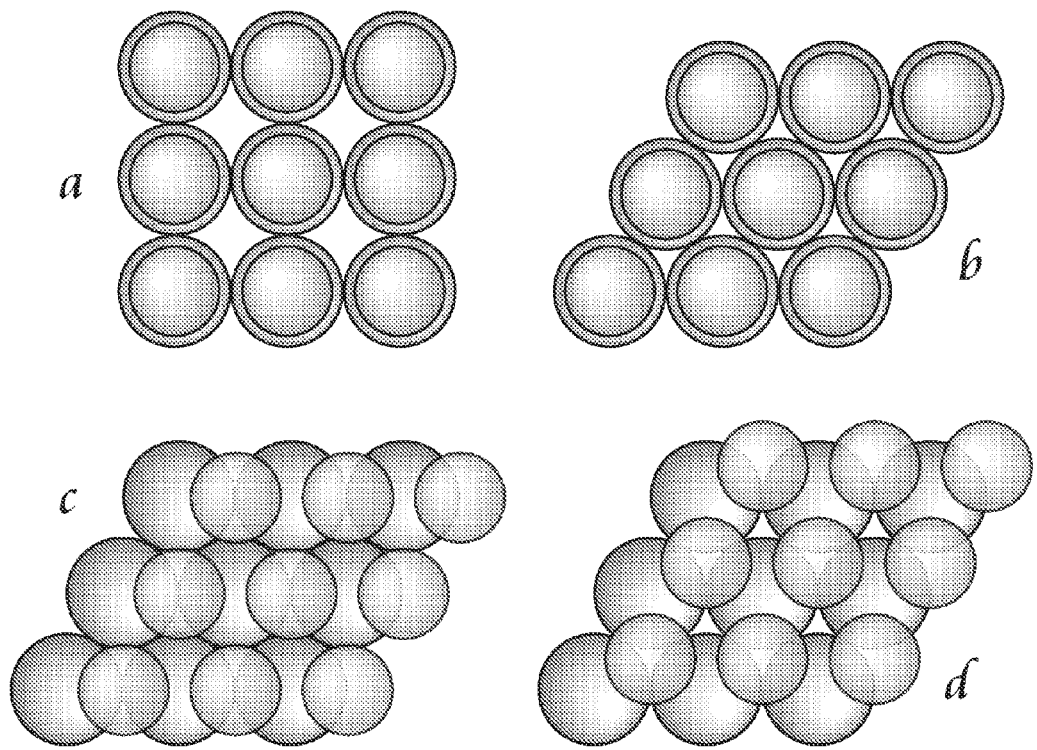
FIGS. 5a, 5b, 5c, and 5d are top views of regular arrangements of spherical porosity in cubic, orthorhombic, tetragonal-spenoidal, and rhombohedral arrangements, respectively, with the top layer of pores intentionally shown smaller for clarity.

Two fundamental types of porous layers of close-packed pores are shown in FIGS. 4a and 4b, and depict the limiting arrangement of 90° and 60° for those respective angles of intersection. There are four unique regular pore arrangements given the assumptions of close packing and the aforementioned angles of intersection. These pore arrangements are generally described as cubic, orthorhombic, tetragonal (or tetragonal-spenoidal), and rhombohedral as noted in FIGS. 5a-5d.

Figure 6:
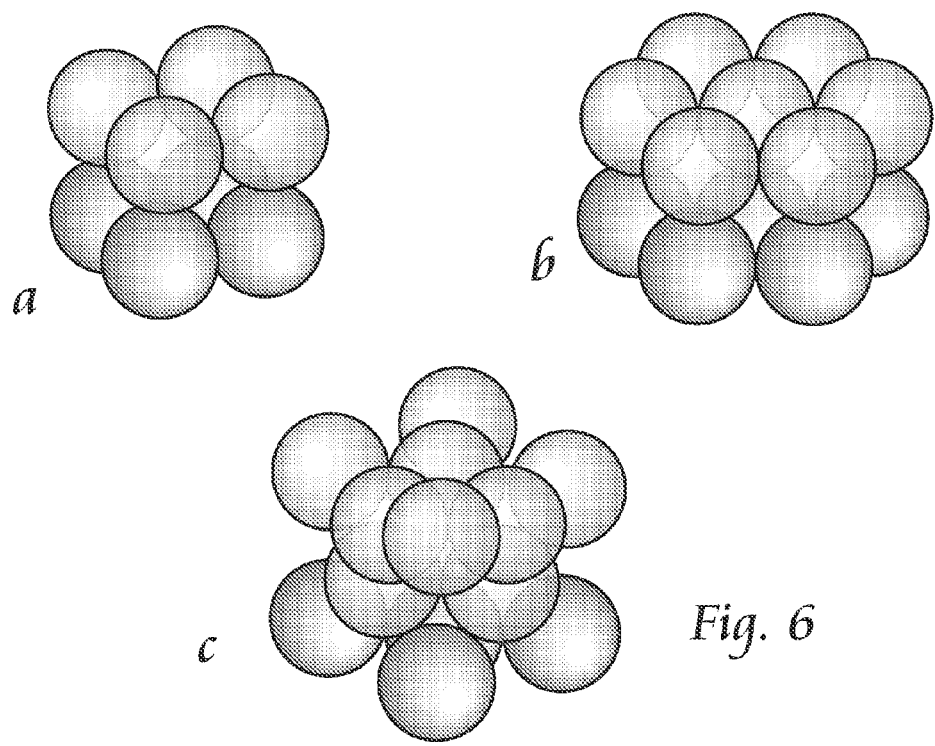
FIGS. 6a, 6b, and 6c are side views of square layer pore arrangements, for simple cubic (SC), hexagonal prismatic (HP) and face-centered cubic (FCC) arrangements, respectively.
Figure 7:
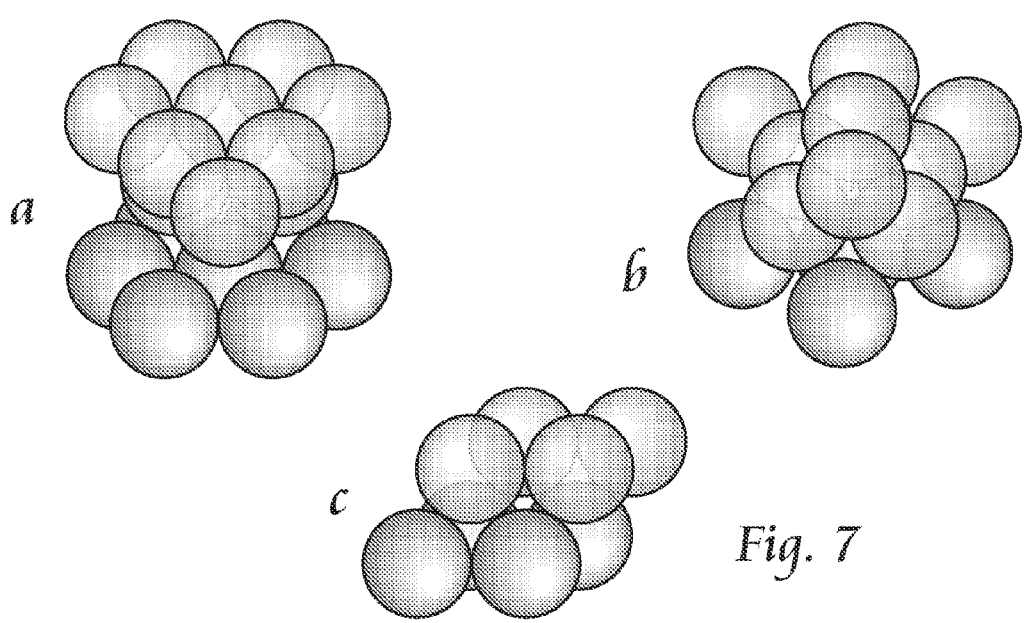
FIGS. 7a, 7b and 7c are rhombic layer pore arrangements in hexagonal close-packed (HCP), FCC, and tetragonal-spenoidal arrangements, respectively.
Figure 8:
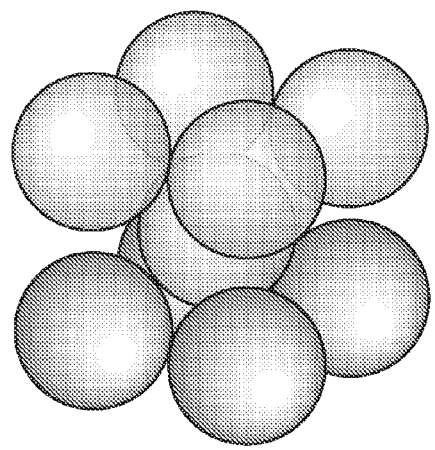
FIG. 8 is a perspective view of a body-centered cubic (BCC) pore arrangement.

The Boolean inverse of the stacking variations of consecutive square layers of pores, as shown in FIGS. 6a-6c, results in the generation of simple cubic (SC), hexagonal prismatic (HP) or face-centered cubic (FCC) unit cells. The stacking of consecutive rhombic or triangular layers of pores, as shown in FIGS. 7a-7c, leads to the generation of tetragonal prismatic, HCP and FCC unit cells, as well as the HP cell described previously. The Boolean inverse of one non-close packed pore arrangement, as shown in FIG. 8, results in a body-centered cubic (BCC) unit cell and is also included in the invention The porosity parameters of these five unit cells are summarized in Table 1. The variable r is the pore radius, L is the resulting center-to-center dimension between the nearest adjacent pores for a given unit cell structure, and ψ is the ratio of r/L. The maximum porosity of each unit cell occurs when the ratio ψ equals 0.5.

TABLE 1

Summary of porosity for modeled unit cells.

| | Unit cell | Figure | Porosity relationship as function of r, L and ψ ratio | | Maximum porosity |
|---|---|---|---|---|---|
| Square close-packed layers (FIG. 4a) | SC | 4.5a | $[4(\frac{1}{3})\pi r^3]/L^3$ | $4.18879 (\psi)^3$ | 52.4% |
| | HP | 4.5b | $(4\pi r^3)/1.5\sqrt{3} L^3$ | $4.83679 (\psi)^3$ | 60.5% |
| | FCC | 4.5c | $[16(\frac{1}{3})\pi r^3]/(\sqrt{2})^3 L^3$ | $5.92379 (\psi)^3$ | 74.1% |
| Rhombic close-packed layers (FIG. 4b) | HP | 4.5b | $(4\pi r^3)/1.5\sqrt{3} L^3$ | $4.83679 (\psi)^3$ | 60.5% |
| | Tetragonal-sphenoidal | 4.6c | N/A | | |
| | HCP | 4.6a | $(8\pi r^3)/\sqrt{18} L^3$ | $5.92384 (\psi)^3$ | 60.5% |
| | FCC | 4.6b | $[16(\frac{1}{3})\pi r^3]/(\sqrt{2})^3 L^3$ | $5.92379 (\psi)^3$ | 74.1% |
| Non-close packed | BCC | 4.7 | $(\sqrt{3}) \pi r^3/L^3$ | $5.44141 (\psi)^3$ | 68.0% |

Figure 9:
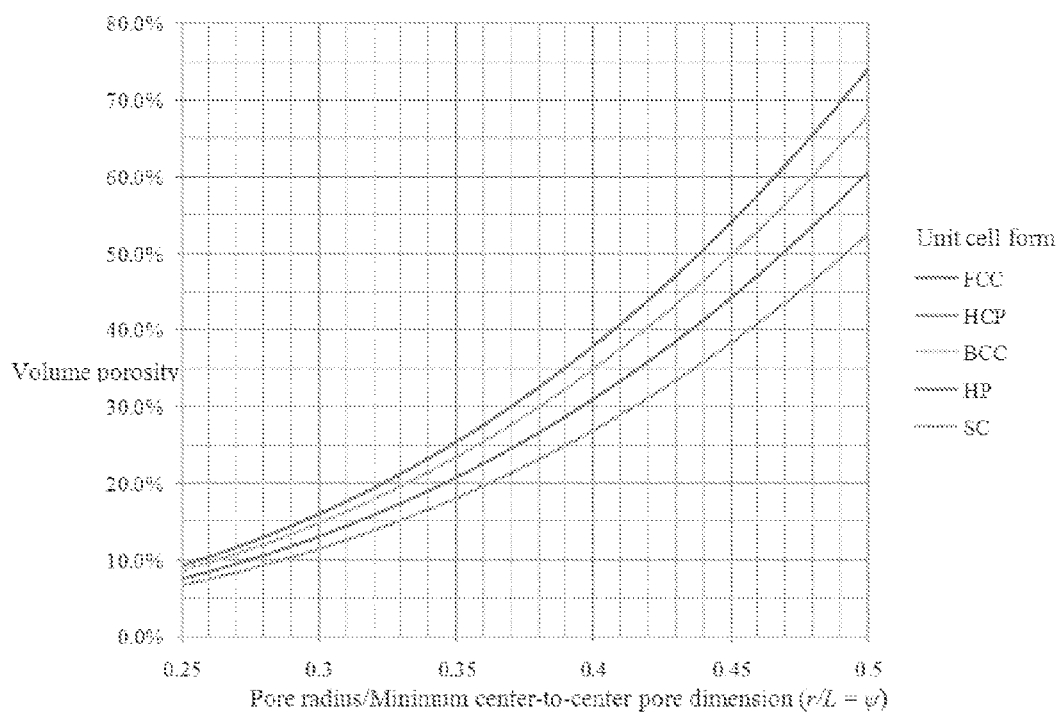
FIG. 9 is a chart showing porosity versus ψ for different unit cells.

Without limiting the scope of the invention, those pore arrangements most likely to be of clinical relevance to the design of orthopaedic implants have been identified. Irrespective of pore arrangement, increases in volume porosity result in decreases in Young's modulus. FIG. 9 shows the relative changes in volume porosity as a function of pore radius/minimum center-to-center pore dimension, ψ (r/L), for various unit cells. As also seen in FIG. 9, Porosity versus ψ for different unit cells is shown. For a given porosity design (i.e., specification of pore size and minimum center-to center dimension), the FCC, HCP and BCC unit cells yield the largest volume porosity and offer the greatest potential reduction in effective Young's modulus, defined as $E_{porous}/E_{solid}$.

It is noted that spherical pores are preferred, but other pore shapes can be produced in non-spherical patterns, such as cubes, cuboids, and other three-dimensional pore geometries such as cylinders, cubes, dodecahedron, etc., torus (doughnut), ellipsoid, spheroid, hyperboloid, paraboloid, etc. can be produced.

Figure 10:
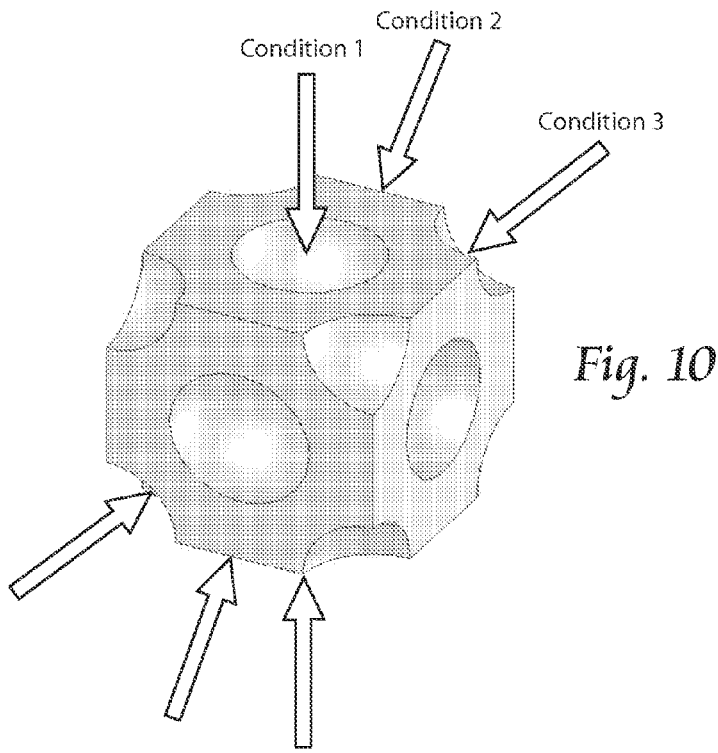
FIG. 10 is a visualization of representative loading conditions for FCC unit cell; <010>: condition 1, <110>: condition 2, and <111>: condition 3.

Given that the unit cells that result from the previously described pore arrangements have either a cubic or hexagonal prismatic shape, only a limited number of practical symmetric loading configurations exist. In the instance of those with a cubic shape (FCC or BCC unit cells), loads can be applied to opposing parallel faces of the unit cell (load condition 1), a loading scenario analogous to a <010> crystallographic orientation using Miller indices. Similarly, load can be applied to diagonally opposite edges of the regular cubic structure (load condition 2) or a <110> orientation. It is also conceivable that load can be applied to the diagonally opposite corners of these cubic unit cells (load condition 3) or a <111> orientation. FIG. 10 shows these representative loading conditions on the FCC unit cell.

Figure 11:
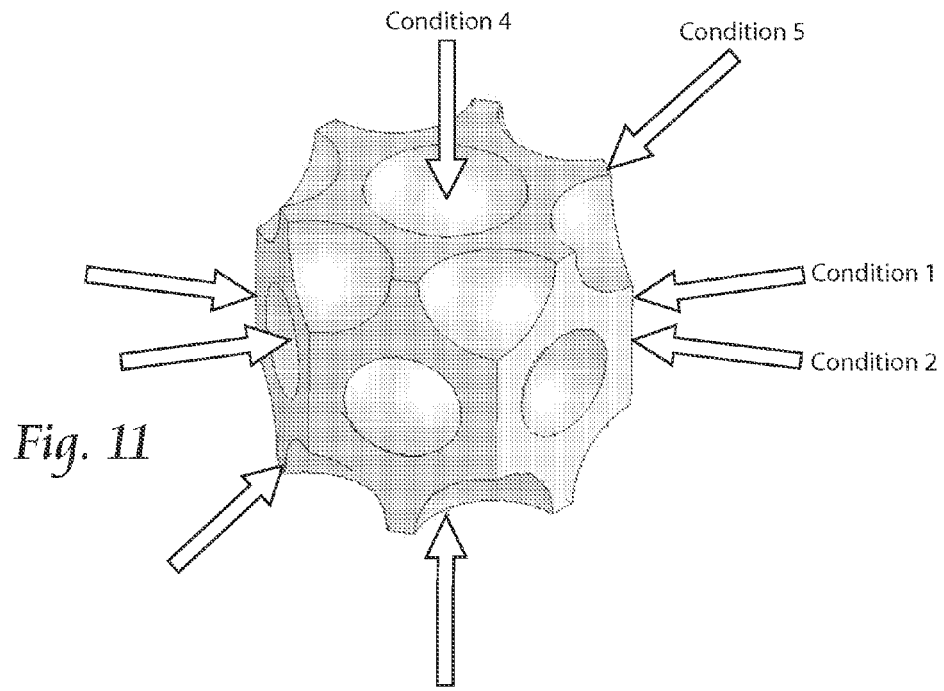
FIG. 11 is a visualization of representative loading conditions for HCP unit cell; condition 1, condition 2, condition 4 and condition 5.

In the case of unit cells that have a hexagonal prismatic shape, such as HCP unit cells, load can be applied to the opposing parallel rectangular faces of the prism (load condition 1) or to the opposing parallel hexagonal faces (load condition 4). It is also possible for the unit cell to be oriented such that load is applied along the diagonally opposite edges of the hexagonal faces (load condition 5) or the opposing parallel edges of the rectangular sides of the hexagonal prism (load condition 2). FIG. 11 shows the representative loading conditions on the HCP unit cell. Each vector in FIGS. 10 and 11 represents the resultant force over the corresponding surface, edge or corner of the unit cell.

The invention includes the creation of solid models representing each loading condition from a large assemblage of individual unit cells using computer-aided design (CAD) software. Planes are inserted at critical locations through the assembly so as to create and isolate an RVE that represents the desired loading orientation on a specific microstructure.

A finite element (FE) model corresponding to each RVE was defined in terms of element selection, material properties, mesh design, applied loads, boundary conditions and model size/scaling factors. The number of unit cells within the FE model can be deemed sufficiently large once periodicity in the response is observed within a central sub-domain of the RVE, both in the direction of the load and across a plane perpendicular to the applied load. Additional boundary conditions were applied such that the modeled RVE approximates the continuum of the periodic microstructure. To obtain an accurate estimation of elastic constants, the results of two numerical analyses are averaged. These analyses include a "free" or laterally unconstrained boundary condition (BC1) and a "continuum" boundary condition (BC2). BC1 imposes uniform displacements corresponding to 1% uniaxial strain on the faces of the RVE perpendicular to the loading direction without friction; the (unloaded) faces parallel to the loading direction are traction free. BC2 imposes the same conditions on the faces perpendicular to the loading direction. However, the faces parallel to the loading direction are constrained to remain planar and parallel during deformation, thereby applying traction to the planar faces and simulating an interior domain. These boundary conditions provide oppositely biased responses and that the mean of the individual simulations under these two boundary conditions approximate the continuum such that small models can obtain convergent results equivalent to larger models of the same regular porous structure.

For a preferred embodiment, a minimum pore separation of 500 μm was selected as current AM processes cannot consistently reproduce smaller geometric features. The desired porosity range was determined by estimating the effective modulus ($E_{porous}/E_{solid}$) needed for a Ti6Al4V implant to approximate the Young's modulus of cortical bone (~20 GPa). Given a Young's modulus for Ti alloy (E~114 GPa), this effective modulus is approximately 0.20. Existing mechanical property-porosity relationships suggest that the porosity needed for an effective modulus of 0.20 is in the range of 20-50%. While this effective modulus does not consider tensile or fatigue strength concerns, this porosity range is sufficient to define the invention.

The initial research specified pore radii/separation parameters that were realistic in terms of current AM capabilities and bracketed the volume porosity range (20-50%) most likely to be of clinical significance. Any pore separation in excess of the minimum achievable pore spacing reduces porosity and increases the effective Young's moduli. Accordingly, design refinements focused on the effect of changes in microstructure and pore radius on Young's modulus and Poisson's ratio at the minimum pore spacing of 500 μm.

Figure 12:
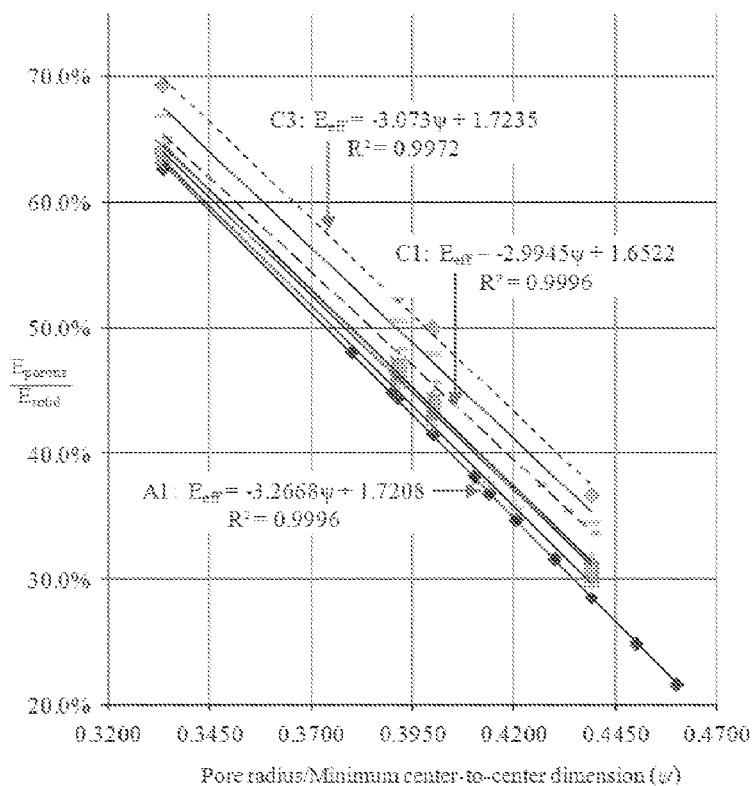
FIG. 12 is a chart showing FEA Data for Effective Modulus as a function of ψ for different structures and loading conditions.

All regression lines for Young's modulus as a function of ψ fall within the band defined by those of RVEs A1 and C1 in FIG. 12. The results for Poisson's ratio shown in FIG. 13 are banded by the regression lines for RVEs A1 and C3.

Figure 13:
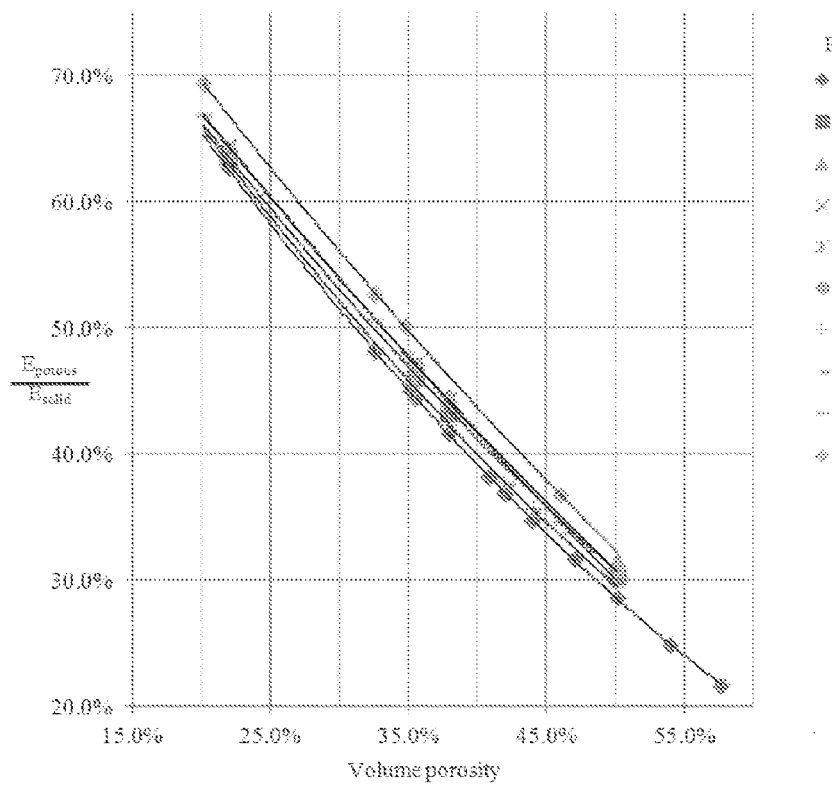
FIG. 13 is a chart showing FEA Data for Effective Modulus a function of volume porosity (P) for different structures and loading conditions.

As seen in FIGS. 12 and 13, the effective Young's modulus varies linearly with ψ. The data designation A refers to the FCC unit cell, B to the HCP unit cell and C, the BCC unit cell in all figures. The numeric designation after each letter refers to the loading direction shown in FIGS. 10 and 11. The relationship between Poisson's ratio and ψ and volume porosity appears second order.

These data show that the response of a specific microstructure changes as the direction of the applied load is varied. The equations resulting from the regression analysis of the FE data for Young's modulus and Poisson's ratio are summarized in Table 2.

TABLE 2

Equations for effective moduli as a function of ψ

| Structure | $E_{eff} = f(\psi)$ | $\nu = f(\psi)$ for Ti6Al4V | Porosity = $f(\psi)$ |
|---|---|---|---|
| A1 | $-3.267\psi + 1.721$ | $1.561\psi^2 - 1.230\psi + 0.552$ | $5.924\,\psi^3$ |
| A2 | $-3.141\psi + 1.686$ | $0.860\psi^2 - 0.826\psi + 0.490$ | $5.924\,\psi^3$ |
| A3 | $-3.039\psi + 1.655$ | $0.812\psi^2 - 0.874\psi + 0.507$ | $5.924\,\psi^3$ |
| B1a | $-3.173\psi + 1.707$ | $0.531\psi^2 - 0.608\psi + 0.454$ | $5.924\,\psi^3$ |
| B2a | $-3.112\psi + 1.677$ | $0.689\psi^2 - 0.715\psi + 0.469$ | $5.924\,\psi^3$ |
| B4a | insufficient data | insufficient data | $5.924\,\psi^3$ |
| B5a | $-3.185\psi + 1.696$ | $0.921\psi^2 - 0.853\psi + 0.493$ | $5.924\,\psi^3$ |
| C1 | $-2.995\psi + 1.652$ | $0.250\psi^2 - 0.318\psi + 0.394$ | $5.441\,\psi^3$ |
| C2 | $-3.039\psi + 1.688$ | $0.929\psi^2 - 0.884\psi + 0.503$ | $5.441\,\psi^3$ |
| C3 | $-3.073\psi + 1.724$ | $1.168\psi^2 - 1.182\psi + 0.580$ | $5.441\,\psi^3$ |

These equations indicate that the determination of Young's modulus is affected by direction of applied load and that porous microstructures of the type evaluated in this study are not isotropic. Regardless of a specific ψ value or the volume porosity of the microstructure, loading on the face of the FCC structure (load condition 1) consistently yields the lowest value for Young's modulus. This result suggests that the preferred embodiment should utilize this loading orientation and microstructure to obtain moduli that offer the greatest potential for reduction in bone resorption.

Research indicates that the selection of microstructure (FCC, HCP, or BCC) has only a minimal effect on the resulting Young's modulus. However, different microstructures subjected to identical loading conditions yield measurably different results for Poisson's ratio.

The linear relationship between the effective Young's modulus and ψ is robust, with all of the respective microstructures described by regression equations having a coefficient of determination ($R^2$) greater than 0.99. A second order equation defines the relationship between ψ and Poisson's ratio for a given microstructure but the variation in Poisson's ratio as porosity and ψ increase for structures other than the FCC requires further investigation. Research also demonstrates that the mechanical properties of porous constructs can be tailored with the appropriate selection of orientation to the applied load, microstructure (in the case of Poisson's ratio only) and porosity or ψ level.

There are distinct advantages in keeping any implant entirely metallic, including biocompatibility, ease of fabrication, a proven history of use and existing FDA approval considerations. However, although implant manufacturers have long promoted some alloys as a "less stiff" material, metal alloys used for implant applications have elastic moduli seven to fourteen times greater than that of cortical bone and 200 to 400 times greater than that of cancellous bone.

While a variety of different processes for the production of open-cell porous metals exist, the production of closed-cell porous materials is limited to gas injection or the decomposition of foaming agents in molten metal, both of which produce random pore distributions. Additionally, the size and shape of the resulting pores in the matrix varies depending on the parameters of the manufacturing process. While these methods are commonly used to produce aluminum, zinc and magnesium foams, they are not suitable for the production of closed-cell titanium because of the high melting temperatures involved and the associated reactivity of titanium with oxygen in the melt. Relative to the manufacture of orthopaedic implants, accurate control over production processes for closed-cell metals is readily attained only through additive manufacturing (AM) techniques which use layer-by-layer fabrication technologies.

Aside from manufacturing concerns, the design of closed-cell structures that incorporate an engineered distribution of internal pores is further complicated by the absence of robust correlations between specific porous microstructures and the resulting moduli.

Relationships between key design parameters (i.e., pore size, pore separation and stacking arrangement) led to the equations in Table 2 that correlate physical modifications of the porous structure to the effective moduli of the resulting construct. In general, these results are consistent with existing research on the mechanical properties of porous materials showing that Young's modulus has an inverse relationship with increases in porosity. Since the metallic alloys used in implant applications have significantly larger Young's moduli than cortical bone, those pore arrangements that yielded the largest reduction in modulus at a given porosity have the greatest potential clinical relevance to orthopaedic implant design.

The FE results indicated that for any given $\psi$, the ratio of pore radius to the center-to-center pore dimension, or volume porosity, the FCC structure with face-centric loading predicted the greatest reduction in Young's modulus over a porosity range of 20-50%. As such, porous constructs (a preferred embodiment) for fabrication and subsequent physical testing incorporate the FCC pore arrangement with unit cells oriented such that tensile and/or compressive loads are applied normal to the faces of the cells.

To design the porous prototype, the desired Young's modulus and Poison's ratio is identified. As shown in Table 2, the effective Young's modulus ($E_{eff}$) and Poisson's ratio ($\nu_{eff}$) for an FCC structure with loading normal to the faces of the unit cells is predicted by the following equations:

$$(E_{porous}/E_{solid}) = E_{eff} = -3.267\psi + 1.721$$

$$\nu_{eff} = 1.561\psi^2 - 1.230\psi + 0.552$$

where $\psi$ is the ratio of pore radius, r, to the center-to-center pore dimension, L. These equations are applicable to a $\psi$ range of 0.3333 to 0.4600 and $\nu$ assumes the use of a titanium alloy with $\nu_{Ti}$ of 0.342.

As spinal rods have a uniform cylindrical cross section and are typically available in sizes from 4.5 through 6.35 mm in diameter, a prototypical 6.35 mm diameter spinal rod was selected for design and fabrication. This diameter allowed the inclusion of internal pores that were large enough to be accurately produced by commercially available AM processes.

As the use of a fully porous construct could potentially result in a stress concentration associated with a surface pore near the point of load, a solid exterior or superficial metallic layer was included in the design of the prototypical rod. Accordingly, a 0.5 mm solid layer, a practical AM limit based on examination of representative photomicrographs, was incorporated in the design, leaving a 5.35 mm diameter inner cylindrical section for the porous structure. To achieve maximum porosity within these geometric constraints, a 0.725 mm pore radius was an optimal pore size for the inner core of the rod. This dimension allowed a pore separation (solid material between pores) of 0.5 mm and resulted in a center-to-center pore dimension, L, of 1.95 mm. These pore size and center-to-center pore dimensions for the FCC structure correspond to $\psi = r/L = 0.3718$ and a calculated volume porosity of 29.5% for the porous core.

Substitution of this value for $\psi$ in the predictive equations (1) and (2) for effective Young's modulus and Poisson's ratio yields:

$$(E_{porous}/E_{solid}) = E_{eff} = 0.506$$

and $$E_{porous} = 0.506\, E_{Ti6Al4V} = 57.6 \text{ GPa}$$

where Young's modulus of solid Ti6Al4V, $E_{Ti6Al4V}$, is 113.8 GPa, and $$\nu_{eff} = 0.311$$

Figure 14:
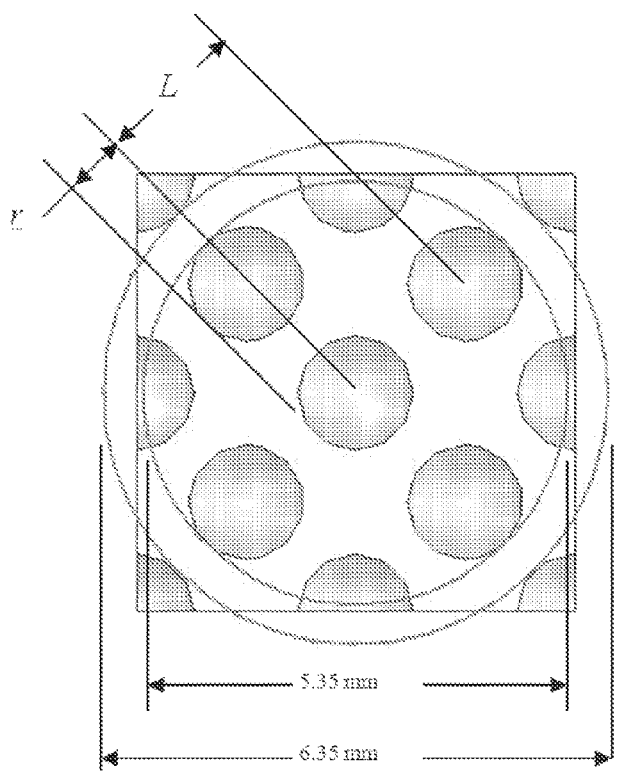
FIG. 14 is an end view of rod with inner and outer diameters of the prototype rod shown superimposed on the FCC porous structure.

FIG. 14 shows the cross-sectional view of the basic porous structure along with key dimensions of the porous core and the resulting rod.

Figure 15:
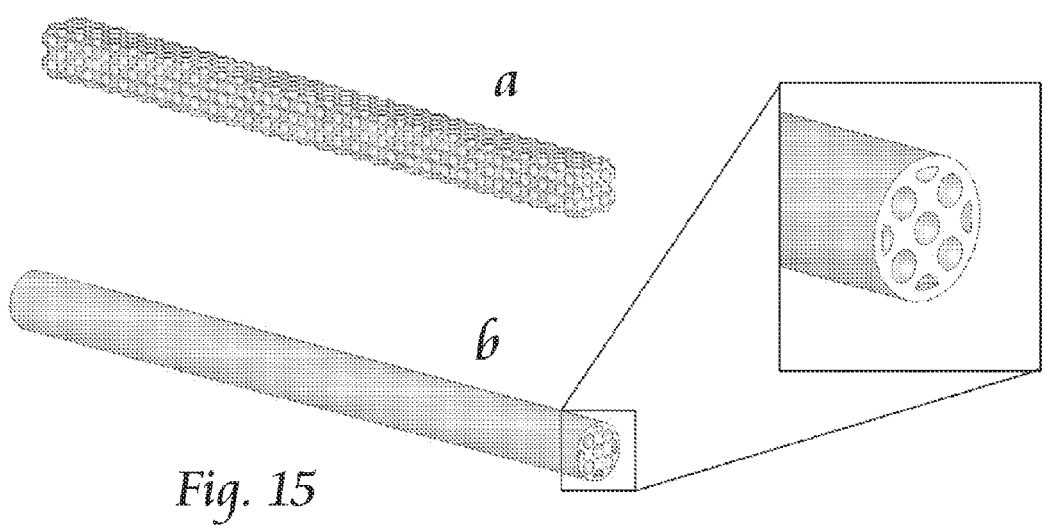
FIGS. 15a and 15b are perspective views, with portions enlarged, of a porous spinal rod, show a basic porous inner structure, and final geometry (bottom and inset) after extrusion and addition of the solid outer layer, respectively.

Forty-eight FCC unit cells with a side length of 2.76 mm were combined and oriented along the long axis of the rod, resulting in a porous construct 132.4 mm in length. FIG. 15 shows the detail of the final solid model including the fully porous structure and after extrusion and incorporation of the porous core within the solid outer layer. A three-dimensional solid model of the desired geometry is created using computer-aided design (CAD) software. The resulting design file, saved in an STL format, becomes the input to the AM machine which decomposes the three-dimensional object into a stack of two-dimensional layers with a nominal thickness of 20-100 µm (depending on the AM system), a process analogous to the generation of a computed tomography (CT) scan in a clinical setting.

In the production of a metallic component, titanium or other metal powders with diametrical size of 10-100 µm is spread across a build surface and a $CO_2$ laser or electron beam is focused onto the powder layer and selectively melts the material, fusing it into a solid sheet. The next powder layer is laid down over the previous, and the process is repeated, creating a solid object with all of the features present in the original CAD file. Because the process proceeds in layer-wise manner, the complexity and detail of the resulting component is limited only by the thickness of the powder layer, the average size of the metal particles and the accuracy and resolution limitations of the machine, typically in the range of ±20-200 µm.

Of greater concern is the ability of these AM systems to generate, within the resolution limits noted, geometrically precise structures as opposed to creating an undefined void within the solid body by a momentary interruption of the laser or electron beam. While this may create a porous material, the resulting microstructure is dependent on the operational characteristics of the machine (e.g., laser or electron beam power, scan spacing and layer thickness) rather than the geometry of a given microstructure. Further, the resulting porous bodies cannot be quantified for potential implant applications except for an estimation of macroscopic bulk properties. For this reason, the invention is limited to the inclusion of pores that are designed into the geometry of the orthopaedic implant (i.e. engineered porosity) and included in the build file that is sent to the AM machine rather than relying on the creation of a porous body by intentional momentary interruption of the energy source.

Relevant research on the achievable size of well-defined pores indicate that diameters within the range of 200 to 700 μm can be produced by, but is not limited to, selective laser melting (SLM), direct metal laser sintering (DMLS), and electron beam melting (EBM). Other currently available AM processes which may practice the invention include direct metal laser sintering (DMLS) and/or laser engineered net shaping (LENS).

Figure 16:
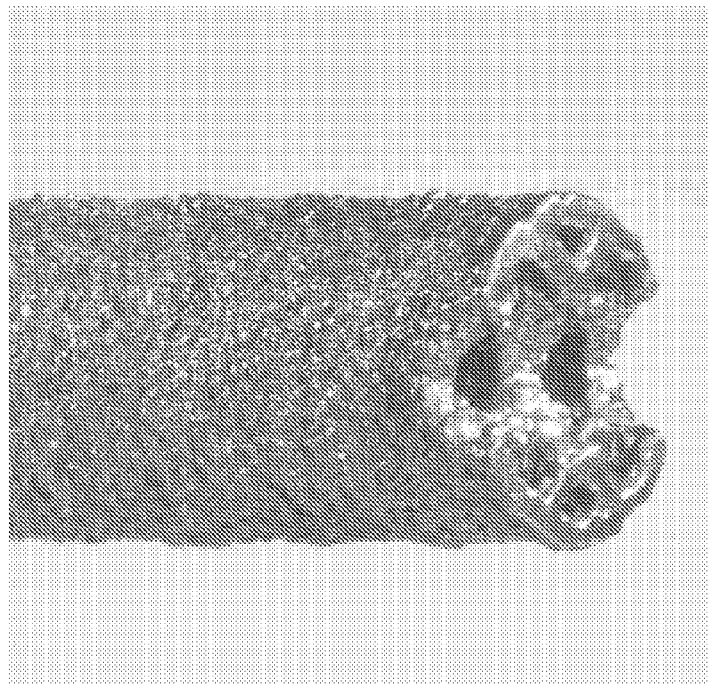
FIG. 16 is an image of a Ti6Al4V spinal rod, EBM techniques.
Figure 17:
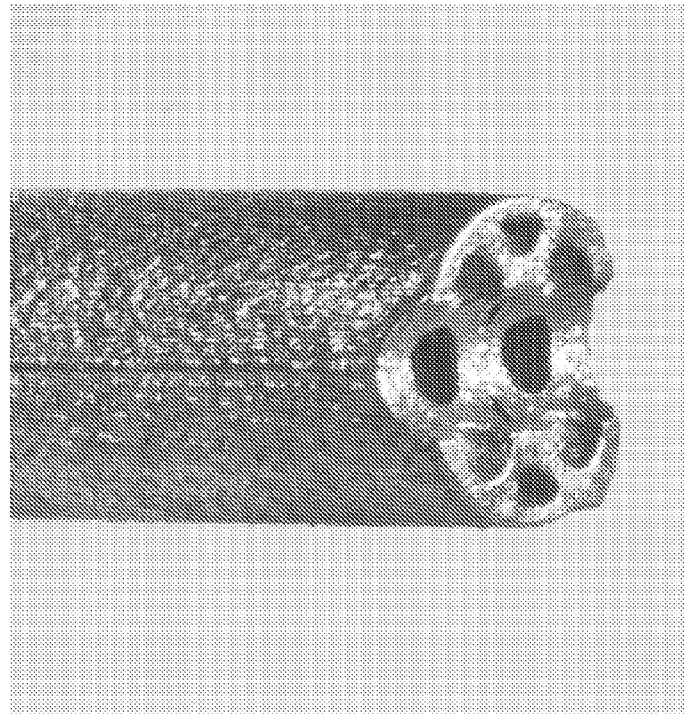
FIG. 17 is an image of a Ti6Al4V spinal rod, with SLM techniques.

Examples of the preferred embodiment were fabricated with Ti6Al4V powder with machine parameters (electron beam or laser power, scan speed, layer thickness and scan spacing) set by the manufacturer. FIGS. 16 and 17 show the resulting porous constructs, partially sectioned to show internal detail, produced by both processes. Implants can be formed with a wide variety of external geometries. One preferred external geometry is a rod-shaped implant, but other geometries can be formed with internal pore structures as previously described. For instance, a flat or curved plate-shaped implant formed by the disclosed methods could be useful in certain implant techniques. Other external geometries can be produced to match or correspond with target sites. For instance, a curved plate could be useful in other portions of a patient's body. Or, external geometries could be constructed to match bone geometries, or portions of bone geometries to match exterior or interior bone shapes.

The results of the 3-point bend test for the solid SLM Ti6Al4V rods yield values for flexural rigidity that agree to within 1.4% of the theoretical calculation with Young's modulus, $E_{Ti6AL4V}$, of 113.8 GPa. For the porous rod, the theoretical estimates of flexural rigidity, (EI) equivalent, assumed a value of 57.6 GPa for Young's modulus of the porous inner core of the designed/fabricated spinal rod, a value based on the predictive equations shown in Table 2.

The experimental 3-point bend test results for the porous SLM Ti6Al4V rod yielded an experimental flexural rigidity of $6.71 \times 10^6$ N-mm2, within 1.6% of the theoretical flexural rigidity determined from application of the proposed predictive equations. These minimal errors confirm the validity of the basic predictive equations for Young's modulus that correlate a specific porous microstructure (FCC pore arrangement) and loading condition (normal to the faces of the unit cubes) with mechanical properties.

The results of the physical testing confirm the validity of the equations proposed to predict the moduli of a specific microstructure and load orientation to within 2% of theoretical over a range of 20-50% porosity. In summary, this method demonstrates that the moduli of porous constructs can be tailored to meet specific clinical needs with the appropriate selection of load orientation, microstructure (in the case of Poisson's ratio only), porosity or ψ level, and the proposed porosity-mechanical property relationships.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A method of forming an implant for insertion in a body, the method comprising:
    selecting a targeted Young's modulus for a portion of said implant,
    selecting a pore arrangement comprising a pore size, a pore separation distance, and a pore structure for said implant to achieve said targeted Young's modulus, said pore structure comprising non-interconnected embedded pores comprising void spaces, said void spaces arranged selected from the group consisting of a simple cubic arrangement, a hexagonal prismatic arrangement, a face-centered cubic arrangement, a hexagonal close-packed arrangement and a body-centered cubic arrangement;
    calculating a predicted Young's modulus of said pore arrangement, comparing said predicted Young's modulus with said targeted Young's modulus, and, if required, modifying said pore arrangement to substantially achieve said targeted Young's modulus,
    supplying a material comprising individual particles of metallic material;
    bonding said material by at least one of melting, sintering or fusing of said particles into an implant form comprising said selected pore arrangement.

2. An implant formed by the method of claim 1.

3. A method according to claim 1, wherein said implant is rod shaped.

4. A method according to claim 1, wherein said implant is plate shaped.

5. A method according to claim 4, wherein said plate is flat.

6. A method according to claim 4, wherein said plate is curved.

7. A method according to claim 1, said pores having a pore radius between 100 μm to 2000 μm.

8. A method according to claim 1, said method further comprising varying a bending stiffness or a flexural rigidity of said implant by varying at least one of a pore radius, a minimum center-to-center distance between adjacent pores, and an orientation of the specific arrangement of pores relative to an applied load.

9. A method according to claim 1, wherein said pores are spherical.

* * * * *